United States Patent [19]

Barth et al.

[11] Patent Number: 5,624,941

[45] Date of Patent: Apr. 29, 1997

[54] PYRAZOLE DERIVATIVES, METHOD OF PREPARING THEM AND PHARMACEUTICAL COMPOSITIONS IN WHICH THEY ARE PRESENT

[75] Inventors: Francis Barth; Pierre Casellas, both of Montpellier; Christian Congy, Saint Gely du Fesc; Serge Martinez, Montpellier; Murielle Rinaldi, Saint Georges d'Orques; Gilles Anne-Archard, Toulouse, all of France

[73] Assignee: Sanofi, Paris, France

[21] Appl. No.: 348,881

[22] Filed: Nov. 29, 1994

Related U.S. Application Data

[63] Continuation-in-part of Ser. No. 168,237, Dec. 17, 1993, abandoned, which is a continuation-in-part of Ser. No. 79,870, Jun. 23, 1993, abandoned.

[30] Foreign Application Priority Data

| Jun. 23, 1992 | [FR] | France | 92 07645 |
| Dec. 2, 1993 | [FR] | France | 93 14444 |
| Jul. 20, 1994 | [FR] | France | 94 08974 |

[51] Int. Cl.$^6$ .................................... A61K 31/445
[52] U.S. Cl. .............. 514/326; 514/212; 514/236.5; 514/341; 514/404; 514/406; 514/407; 544/127; 546/247; 546/211; 548/357.5; 548/364.1; 548/364.7; 548/371.7; 548/372.5; 548/374.1; 548/375.1
[58] Field of Search ............... 546/211, 247; 548/374.1, 364.4, 357.5, 364.1, 364.7, 375.1, 371.7, 372.5; 544/127; 514/212, 236.5, 326, 341, 404, 406, 407

[56] References Cited

U.S. PATENT DOCUMENTS

| 3,449,350 | 6/1969 | Walker | 546/275.4 |
| 4,826,868 | 5/1989 | Wachter et al. | 514/407 |
| 5,013,837 | 5/1991 | Ward et al. | 544/143 |
| 5,051,518 | 9/1991 | Murray et al. | 548/375.1 |
| 5,134,142 | 7/1992 | Matsuo et al. | 514/255 |
| 5,164,381 | 11/1992 | Wachter et al. | 514/85 |

FOREIGN PATENT DOCUMENTS

| 0029363 | 5/1981 | European Pat. Off. |
| 0248594 | 12/1987 | European Pat. Off. |
| 0293220 | 11/1988 | European Pat. Off. |
| 0418845 | 3/1991 | European Pat. Off. |
| 0445781 | 9/1991 | European Pat. Off. |
| 0477049 | 3/1992 | European Pat. Off. |
| 0576357 | 12/1993 | European Pat. Off. |

OTHER PUBLICATIONS

Boyd et al., *Journal of the Chemical Society, Perkin Transactions 1*, vol. 21, 1973, pp. 2532–2535.

Fusco et al., *Tetrahedron Letters*, No. 46, 1967, pp. 4541–4544.

CA110:75489 (Feb. 1989).

*Primary Examiner*—Brian M. Burn
*Attorney, Agent, or Firm*—Bacon & Thomas

[57] ABSTRACT

The present invention relates to compounds of the formula:

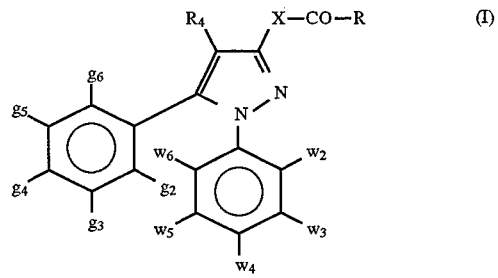

These compounds are useful in pharmaceuticals in which cannabis is known to be involved.

30 Claims, No Drawings

PYRAZOLE DERIVATIVES, METHOD OF PREPARING THEM AND PHARMACEUTICAL COMPOSITIONS IN WHICH THEY ARE PRESENT

The present application is a continuation-in-part application of U.S. Ser. No. 08/168,237, filed Dec. 17, 1993, now abandoned, which is a continuation-in-part application of U.S. Ser. No. 08/079,870, filed Jun. 23, 1993, now abandoned.

The present invention relates to novel pyrazole derivatives, to a method of preparing them and to the pharmaceutical compositions in which they are present.

Numerous pyrazole derivatives have been described in the literature; more particularly, EP-A-268554 and DE-A-3910248 claim pyrazoles possessing herbicidal properties, EP-A-430186 and JP-A-03031840 claim compounds useful for photography, and EP-A-418845 claims pyrazoles possessing antiinflammatory, analgesic and antithrombotic activity.

It has now been found that the pyrazoles forming the subject of the invention have a good affinity for the cannabinoid receptor and are therefore particularly valuable in the therapeutic areas in which cannabis is known to be involved.

$\Delta^9$-Tetrahydrocannabinol, or $\Delta^9$-THC, is the main active constituent extracted from *Cannabis sativa* (Tuner, 1985; In Marijuana 84, Ed. Harvey, D. Y., IRL Press, Oxford).

The effects of cannabinoids are due to an interaction with specific high-affinity receptors present in the central nervous system (Devane et al., Molecular Pharmacology, 1988, 34, 605–613) and peripheral nervous system (Nye et al., The Journal of Pharmacology and Experimental Therapeutics, 1985, 234, 784–791; Kaminski et al., 1992, Molecular Pharmacology, 42, 736–742; Munro et al., Nature, 1993, 365, 61–65).

Characterization of this receptor has been made possible by the development of specific synthetic ligands such as the agonists WIN 55212-2 (J. Pharmacol. Exp. Ther., 1993, 264, 1352–1363) or CP 55,940 (J. Pharmacol. Exp. Ther., 1988, 247, 1046–1051).

The therapeutic indications of cannabinoids pertain to a variety of areas such as the immune system, the central nervous system and the cardiovascular or endocrine system (Hollister, Pharmacological Reviews, 1986, 38, 1–20, Renv and Sinha, Progress in Drug Research, 1991, 36, 71–114, Cannabinoid receptor expression in human leucocytes, European Journal of Biochemistry, 1993, 214, 173–180.

More particularly, compounds possessing an affinity for the cannabinoid receptor are useful as Immunomodulators and psychotropic agents, in thymic disorders, vomiting, myorelaxation, various types of neuropathy, memory disorders, dyskinesia, migraine, asthma, epilepsy and glaucoma or else in anticancer chemotherapy, in ischemia and angor, in orthostatic hypotension and in cardiac insufficiency.

Thus, according to one of its features, the present invention relates to the compounds of the formula

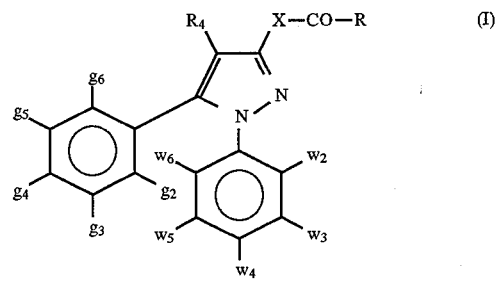

in which $g_2$, $g_3$, $g_4$, $g_5$ and $g_6$ and $w_2$, $w_3$, $w_4$, $w_5$ and $w_6$ are identical or different and are independently hydrogen, a chlorine or bromine atom, a $(C_1-C_3)$-alkyl, a $(C_1-C_3)$ alkoxy, a trifluoromethyl or a nitro group and $g_4$ is optionally a phenyl group;

$R_4$ is hydrogen or a $(C_1-C_3)$-alkyl;

X is either a direct bond or a group $—(CH_2)_xN(R_3)—$, in which $R_3$ is hydrogen or a $(C_1-C_3)$-alkyl and x is zero or one; and R is a group $—NR_1R_2$ in which $R_1$ and $R_2$ are independently a $(C_1-C_6)$-alkyl; an optionally-substituted non-aromatic $(C_3-C_{15})$ carbocyclic radical; an amino $(C_1-C_4)$ alkyl group in which the amino is optionally disubstituted by a $(C_1-C_3)$-alkyl; a cycloalkyl-$(C_1-C_3)$ alkyl in which the cycloalkyl is $C_3-C_{12}$; a phenyl which is unsubstituted or monosubstituted or polysubstituted by a halogen, by a $(C_1-C_5)$-alkyl or by a $(C_1-C_5)$-alkoxy; a phenyl $(C_1-C_3)$-alkyl; a diphenyl-$(C_1-C_3)$-alkyl; a naphthyl; an anthracenyl; a saturated 5- to 8-membered heterocyclic radical which is unsubstituted or substituted by a $(C_1-C_3)$-alkyl, by a hydroxyl or by a benzyl group; a 1-adamantylmethyl; an aromatic heterocycle unsubstituted or mono-or-polysubstituted by a halogen, a $(C_1-C_5)$alkyl, a $(C_1-C_5)$-alkoxy; a $(C_1-C_3)$-alkyl substituted by an aromatic heterocycle unsubstituted or mono- or -polysubstituted by a halogen, a $(C_1-C_5)$ alkyl, a $(C_1-C_5)$-alkoxy, or else $R_1$ is hydrogen and $R_2$ is as defined above, or else $R_1$ and $R_2$, together with the nitrogen atom to which they are bonded, form a saturated 5- to 8-membered heterocyclic radical, said heterocyclic radical being other than morpholine when $w_2$, $w_3$, $w_4$, $w_5$ and $w_6$ and $g_2$, $g_3$, $g_4$, $g_5$ and $g_6$ are all hydrogen;

a group $R_2$ as defined above when X is $—(CH_2)_xN(R_3)—$; or a group $R_5$ when X is a direct bond, $R_5$ being a $(C_1-C_3)$-alkyl; a $(C_3-C_{12})$-cycloalkyl which is unsubstituted or substituted by a $(C_1-C_5)$-alkyl; a phenyl-$(C_1-C_3)$-alkyl which is unsubstituted or substituted by a halogen or by a $(C_1-C_5)$-alkyl; a cycloalkyl-$(C_1-C_3)$-alkyl in which the cycloalkyl is $C_3-C_{12}$ and is unsubstituted or substituted by a $(C_1-C_5)$-alkyl; or a 2-norbornylmethyl; or one of their salts, where appropriate.

The non-aromatic $C_3-C_{15}$ carbocyclic radicals include saturated or unsaturated, fused or bridged monocyclic or polycyclic radicals, optionally terpene radicals. These radicals are optionally mono- or polysubstituted, said substituent(s) being different from a substituted carbonyl group. Advantageously, the monocyclic radicals are substituted by at least one group selected among the $(C_1-C_5)$ alkyl, $(C_1-C_5)$alkoxy, halogen or hydroxy groups, it being understood that in the case of terpenes or terpene radicals, for example bornyl, menthyl or menthenyl, the alkyl groups of the terpene are not considered as substituents.

The monocyclic radicals include cycloalkyls, for example cyclopropyl, cyclopentyl, cyclohexyl, cycloheptyl, cyclooctyl and cyclododecyl, which are unsubstituted or substituted by at least one $(C_1-C_5)$-alkyl, $(C_1-C_5)$-alkoxy, halogen or hydroxy groups.

The fused, bridged or spiranic dicyclic or tricyclic radicals include for example norbornyl, bornyl, isobornyl, noradamantyl, adamantyl and spiro[5,5]undecanyl, said radicals being unsubstituted or substituted by a $(C_1-C_5)$-alkyl.

Saturated 5- to 8-membered heterocyclic radical is understood as meaning a fused or bridged, non-aromatic monocyclic, dicyclic or tricyclic heterocyclic radical, the heteroatom being S, O or N, or a non-aromatic monocyclic heterocyclic radical containing a nitrogen atom and an oxygen or sulfur atom, said radicals being for example tetrahydrofuranyl, tetrahydrothiofuranyl, tropyl, morpholinyl, thiomorpholinyl, piperidinyl, piperazinyl, pyrrolidinyl or quinuclidinyl, the 1-pyrrolidinyl, 1-piperidinyl, 1-hexahydroazepinyl, 4-morpholinyl and 4-thiomorpholinyl radicals being advantageous.

The aromatic heterocycles can be monocyclic or dicyclic, for example pyrrolyl, pyridyl, indolyl, quinolinyl, thiazolyl or isoindazolyl, these aromatic heterocycles being unsubstituted or substituted for example by halogens, $(C_1-C_5)$-alkyl or $(C_1-C_5)$-alkoxy. The prefered aromatic heterocycles are pyridyl, pyrrole, indole groups, the radicals 2-indolyl or 3-indolyl are particularly prefered.

In formula (I) above, preferably at least one of the substituents $w_2$, $w_3$, $w_4$, $w_5$ and $w_6$ and $g_2$, $g_3$, $g_4$, $g_5$ and $g_6$ is other than hydrogen.

In formula (I) above, when R is a Group —$NR_1R_2$, preferably:

$R_1$ is hydrogen or a $(C_1-C_6)$-alkyl group and $R_2$ is as defined above for (I); or $R_1$ and $R_2$ are each a $(C_1-C_6)$-alkyl group or a $(C_3-C_6)$-cycloalkyl group; or $R_1$ is hydrogen or a $(C_1-C_6)$-alkyl group and $R_2$ is a cycloalkyl-$(C_1-C_3)$-alkyl group in which the cycloalkyl is $C_3-C_{12}$; a non-aromatic $(C_3-C_{15})$ carbocyclic radical which is unsubstituted or substituted as above mentioned; a phenyl which is unsubstituted or monosubstituted or polysubstituted by a halogen, by a $(C_1-C_3)$-alkyl or by a $(C_1-C_3)$-alkoxy; a phenyl-$(C_1-C_3)$-alkyl or a $(C_1-C_3)$alkyl substituted by a 2- or 3-indolyl.

Particularly preferably, when R in formula (I) is a group —$NR_1R_2$, $R_1$ is hydrogen or a $(C_1-C_6)$-alkyl and $R_2$ is a non-aromatic $(C_3-C_{15})$ carbocyclic radical, a cycloalkyl-$(C_1-C_3)$-alkyl in which the cycloalkyl is $C_3-C_6$, or a 2- or 3-indolyl-$(C_1-C_3)$-alkyl.

The preferred alkyl groups are methyl, ethyl, propyl and isopropyl.

In formula (I) above, R is advantageously a group —$NR_1R_2$ preferably selected from the radicals (1) to (74) below.

When $R_1$ and $R_2$, with the nitrogen atom to which they are bonded, are a heterocyclic radical, this is preferably a 5-, 6- or 7-membered saturated heterocycle and can contain another heteroatom, especially oxygen or sulfur, for example a pyrrolidine, a piperidine, a hexahydroazepine, a morpholine or a thiomorpholine, with the limitation specified above.

The radicals represented by R as defined for (I) are preferably radicals selected from:

(1) propylamino
(2) butylamino
(3) isopropylamino
(4) dipentylamino
(5) 2-(N,N-diethylamino)ethylamino
(6) benzylamino
(7) 2-phenylethylamino
(8) 3-phenylpropylamino
(9) 3,3-diphenylpropylamino
(10) phenylamino
(11) 3-chlorophenylamino
(12) 4-methylphenylamino
(13) cyclopropylamino
(14) cyclopentylamino
(15) cyclohexylamino
(16) cycloheptylamino
(17) cyclooctylamino
(18) cyclododecylamino
(19) 2-methylcyclohexylamino
(20) 3-methylcyclohexylamino
(21) cis-4-methylcyclohexylamino
(22) trans-4-methylcyclohexylamino
(23) cis-4-tert-butylcyclohexylamino
(24) trans-4-tert-butylcyclohexylamino
(25) 4-hydroxycyclohexylamino
(26) 2-methoxycyclohexylamino
(27) 4-ethylcyclohexylamino
(28) 2,6-dimethylcyclohexylamino
(29) N-methylcyclohexylamino
(30) N,N-dicyclohexylamino
(31) endo-2-norbornylamino (or endo-bicyclo[2.2.1]-heptan-2-amino)
(32) exo-2-norbornylamino (or exo-bicyclo[2.2.1]heptan-2-amino)
(33) 1-adamantylamino
(34) 2-adamantylamino
(35) 1-noradamantylamino
(36) (1R)-bornylamino
(37) (1R)-isobornylamino
(38) spiro[5.5]undecanylamino
(39) cyclohexylmethylamino
(40) 1-adamantylmethylamino
(41) (2-tetrahydrofuranyl)methylamino
(42) 2-(N-methyl-2-pyrrolyl)ethylamino
(43) 2-(2-pyridinyl)ethylamino
(44) (2-indolyl)methylamino
(45) N-methyl(2-indolyl)methylamino
(46) 2-(3-indolyl)ethylamino
(47) N-methyl-2-(3-indolyl)ethylamino
(48) 4-(N-benzylpiperidinyl)amino
(49) 3-quinuclidylamino
(50) exo-bicyclo[3.2.1]octan-2-amino
(51) bicyclo[2.2.2]octan-2-amino
(52) 3-chlorobicyclo[3.2.1]oct-3-en-2-amino
(53) bicyclo[2.2.2]oct-2-en-5-amino
(54) exo-bicyclo[3.2.1]octan-3-amino
(55) endo-bicyclo[3.2.1]octan-3-amino
(56) endo-7-oxabicyclo[2.2.1]heptan-2-amino
(57) exo-7-oxabicyclo[2.2.1]heptan-2-amino
(58) endo-tricyclo[5.2.1.0$^{2,6}$]decan-8-amino
(59) N-ethyl-1-adamantylamino
(60) tricyclo[2.2.1.0$^{2,6}$]heptan-3-amino
(61) bicyclo[3.3.1]nonan-9-amino
(62) endo-1,3,3-trimethylbicyclo[2.2.1]heptan-2-amino (or fenchylamino)

(63) (1R, 2S-endo)-(+)-bicyclo[2.2.1]heptan-2-amino
(64) (1R,2R-exo)-(−)-bicyclo[2.2.1]heptan-2-amino
(65) (1S,2R-endo)-(−)-bicyclo[2.2.1]heptan-2-amino
(66) (1S,2S-exo)-(+)-bicyclo[2.2.1]heptan-2-amino
(67) 1-piperidinylamino
(68) 1-pyrrolidinylamino
(69) 1-hexahydroazepinylamino
(70) 4-morpholinylamino
(71) 4-thiomorpholinylamino
(72) N-methyl-exo-bicyclo[2.2.1]heptan-2-amino
(73) N-ethyl-exo-bicyclo[2.2.1]heptan-2-amino
(74) N-propyl-exo-bicyclo[2.2.1]heptan-2-amino Of the products of formula (I) above, those of formula (Ia) below are advantageous; in particular, the compounds of formula (Ia'):

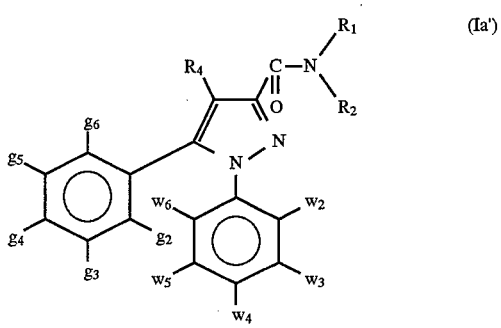

in which $w_2$, $w_3$, $w_4$, $w_5$ and $w_6$, $g_2$, $g_3$, $g_4$, $g_5$ and $g_6$ and $R_4$ are as defined above for (I), $R_1$ is hydrogen or a $(C_1-C_6)$-alkyl and $R_2$ is a non-aromatic $C_3-C_{15}$ carbocyclic radical or a saturated 5- to 8-membered heterocyclic radical selected from 1-pyrrolidinyl, 1-piperidinyl, 1-hexahydroazepinyl, 4-morpholinyl and 4-thiomorpholinyl, and their salts, are particularly advantageous.

Of the products of formula (I), those of formulae (Ia), (Ib), (Ic), (Id), (Ie) and (If) below, in which at least one of the substituents $w_2$, $w_3$, $w_4$, $w_5$ and $w_6$ and $g_2$, $g_3$, $g_4$, $g_5$ and $g_6$ is other than hydrogen, $R_1$ is hydrogen or a $(C_1-C_6)$-alkyl, $R_2$ is as defined above, $R_3$ is hydrogen or a $(C_1-C_3)$-alkyl group, $R_4$ is hydrogen or methyl and $R_5$ is a cycloalkyl-$(C_1-C_3)$-alkyl, the cycloalkyl being $C_3-C_6$, or a phenyl-$(C_1-C_3)$-alkyl which is unsubstituted or substituted on the aromatic ring by a methyl group or a fluorine or chlorine atom, and their salts, where appropriate, are particularly advantageous.

In these latter particularly advantageous products, when $R_1$ is a $(C_1-C_6)$-alkyl, the methyl, ethyl, propyl and isopropyl groups are preferred;

when $R_3$ is a $(C_1-C_3)$-alkyl, the methyl group is preferred;

the preferred groups $R_2$ are non-aromatic $C_3-C_{15}$ carbocyclic radicals which are unsubstituted or substituted by a $(C_1-C_4)$-alkyl, especially methyl, ethyl, propyl, isopropyl or t-butyl, or by two or three methyl groups, for example a methyl-, ethyl- or t-butyl-cyclohexyl radical or a dimethyl- or trimethylcyclohexyl radical, cycloalkyl-$(C_1-C_3)$- alkyl radicals in which the cycloalkyl is $C_3-C_6$; $(C_1-C_3)$-alkyl radicals substituted by a 2- or 3-indolyl group; 2- and 3-indolyl radicals; and 1-pyrrolidinyl, 1-piperidinyl, 1-hexahydroazepinyl, 4-morpholinyl and 4-thiomorpholinyl radicals; and the preferred groups $R_5$ are cyclohexylmethyl, cyclohexylethyl, benzyl, 4-methylbenzyl and phenethyl radicals.

Of the products of formula (I) above, those of formula (i):

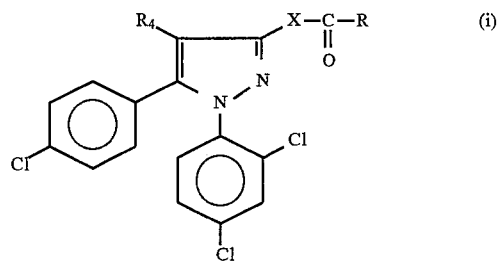

in which $R_4$, X and R are as defined-above for (I), and their salts, are very advantageous, especially when $R_4$ is hydrogen or a methyl group or when $R_4$ is hydrogen or methyl and X is a direct bond.

The compounds of formula (i) in which $R_4$ is hydrogen or methyl, X is a direct bond and R is a group —$NR_1R_2$ in which $R_1$ is hydrogen or a methyl group and $R_2$ is a non-aromatic $C_3-C_{15}$ carbocyclic radical or a saturated 5- to 8-membered heterocyclic radical selected from 1-pyrrolidinyl, 1-piperidinyl, 1-hexahydroazepinyl, 4-morpholinyl and 4-thiomorpholinyl, and their salts, are particularly preferred.

Especially preferred is the compound of formula (i) in which $R_4$ is methyl, X is a direct bond and R is a group —$NR_1R_2$ in which $R_1$ is hydrogen and $R_2$ is 1-piperidinyl, as well as its pharmaceutically acceptable salts and their solvates.

Other particularly preferred compounds of formula (i) are those in which $R_4$ is hydrogen or methyl, X is —$(CH_2)_xN(R_3)$— and R is —$NR_1R_2$, x being zero or one, $R_1$ being hydrogen, $R_3$ being hydrogen or a methyl group and $R_2$ being a phenyl which is unsubstituted or substituted by one or two halogen atoms, a $(C_1-C_5)$-alkyl group or a $(C_1-C_5)$-alkoxy group, or a non-aromatic $C_3-C_{15}$ carbocyclic radical, and their salts.

Of the compounds of formula (I), those of formula (ii):

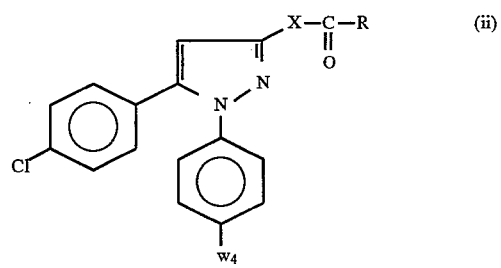

in which X and R are as defined above for (I) and $w_4$ is a methyl or methoxy group, especially those of formula (ii) in which $w_4$ is a methyl or methoxy group, X is a direct bond and R is a group —$NR_1R_2$ in which $R_1$ is hydrogen or a methyl group and $R_2$ is a non-aromatic $C_3-C_{15}$ carbocyclic radical, and their salts, are also advantageous.

An advantageous subclass comprises the compounds of formula (ii) in which $w_4$ is a methyl or methoxy group, X is a group —$(CH_2)_xN(R_3)$— in which x is zero or one and $R_3$ is hydrogen or a methyl group, and R is a group —$NR_1R_2$ in which $R_1$ is hydrogen and $R_2$ is a phenyl which is unsubstituted or substituted by one or two halogen atoms, a $(C_1-C_5)$-alkyl group or a $(C_1-C_5)$-alkoxy group, or a non-aromatic $C_3-C_{15}$ carbocyclic radical, or their salts.

Other valuable compounds according to the present invention are those of formula (I) in which $w_2$, $w_3$, $w_4$, $w_5$ and $w_6$, $g_2$, $g_3$, $g_4$, $g_5$ and $g_6$ and $R_4$ and X are as defined above for (I) and R is a group —$NR_1R_2$ in which $R_1$ is hydrogen or a (C$_1$–C$_6$)-alkyl group and R$_2$ is a 2- or 3-indolyl-(C$_1$–C$_3$)-alkyl group or a 2- or 3-indolyl group, and their salts.

Of the latter, the products of formula (iii):

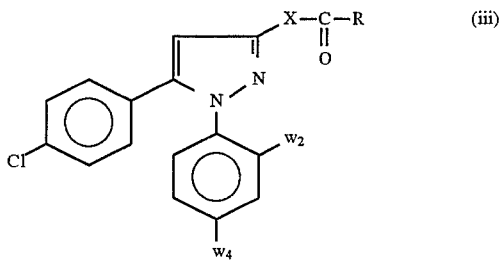

in which X is as defined above for (I), R is a group —NR$_1$R$_2$ in which R$_1$ is hydrogen or a (C$_1$–C$_6$)-alkyl and R$_2$ is a 2- or 3-indolyl-(C$_1$–C$_3$)-alkyl group or a 2- or 3-indolyl group, and either w$_2$ is hydrogen and w$_4$ is a methyl or methoxy group or w$_2$ and w$_4$ are a chlorine atom, and their salts, are particularly valuable.

Of the products included in formula (I) above, those of formula (iv):

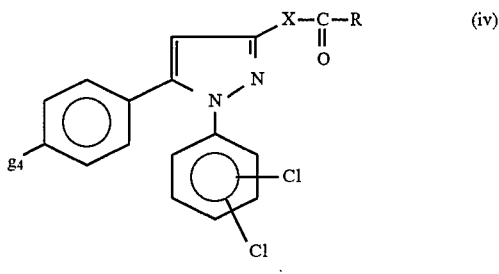

in which X and R are as defined above for (I) and g$_4$ is a bromine atom or a methyl or trifluoromethyl, and their salts, are also valuable.

In preferred products of formula (iv), the two chlorine atoms are in the 2,3-, 2,4-, 2,5- or 3,4-positions, and in these preferred products of formula (iv), those in which X is a direct bond and R is a group —NR$_1$R$_2$ in which R$_1$ is hydrogen or a (C$_1$–C$_6$)-alkyl and R$_2$ is a non-aromatic carbocyclic radical containing from 3 to 15 carbon atoms are particularly preferred.

The salts, where appropriate, of the compounds according to the present invention, especially of those of formulae (I), (Ia'), (i), (ii) and (iii) above and (Ia), (Ib), (Ic), (Id), (Ie) and (If) below, include both those with mineral or organic acids which permit a suitable separation or crystallization of the products, such as picric acid or oxalic acid, and those with acids which form pharmaceutically acceptable salts such as the hydrochloride, hydrobromide, sulfate, hydrogensulfate, dihydrogenphosphate, methanesulfonate, methylsulfate, oxalate, maleate, fumarate, naphthalene-2-sulfonate, glyconate, gluconate, citrate, isethionate and paratoluenesulfonate.

According to another of its features, the present invention relates to a method of preparing the compounds (I), which comprises treating a pyrazole-3-carboxylic acid derivative of the formula

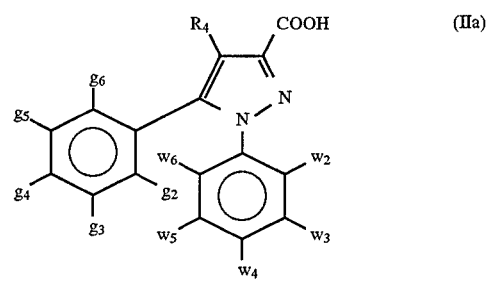

in which w$_2$, w$_3$, w$_4$, w$_5$ and w$_6$, g$_2$, g$_3$, g$_4$, g$_5$ and g$_6$ and R$_4$ are as defined for (I), or one of its activated forms, namely one of its esters or acid chlorides, * either with an amine of the formula HNR$_1$R$_2$, in which R$_1$ and R$_2$ are as defined for (I), to give the amides of the formula

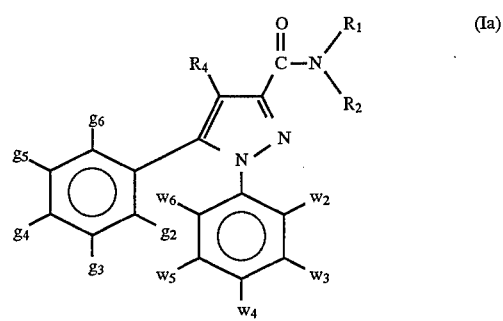

in which w$_2$, w$_3$, w$_4$, w$_5$ and w$_6$, g$_2$, g$_3$, g$_4$, g$_5$ and g$_6$ and R$_4$, R$_1$ and R$_2$ are as defined for (I), * or optionally with a primary amine R$_3$NH$_2$, in which R$_3$ is as defined for (I), to give the intermediate amides (V) of the formula

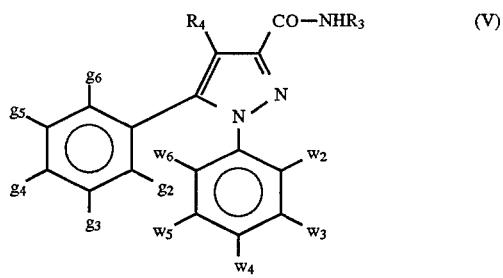

in which w$_2$, w$_3$, w$_4$, w$_5$ and w$_6$, g$_2$, g$_3$, g$_4$, g$_5$ and g$_6$ and R$_4$ and R$_3$ are as defined for (I), to give, by reduction with a metal hydride, the intermediate amines of the formula

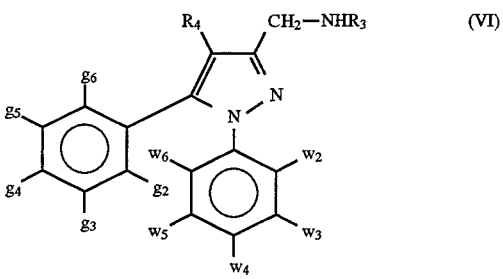

in which w$_2$, w$_3$, w$_4$, w$_5$ and w$_6$, g$_2$, g$_3$, g$_4$, g$_5$ and g$_6$ and R$_4$ and R$_3$ are as defined for (I), which are converted to the amide or urea of the formula

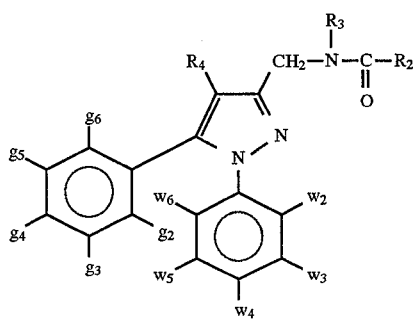

or

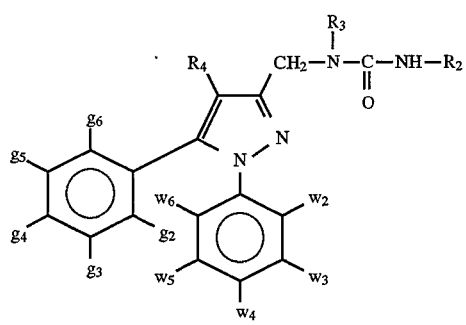

in which $w_2$, $w_3$, $w_4$, $w_5$ and $w_6$, $g_2$, $g_3$, $g_4$, $g_5$ and $g_6$ and $R_2$, $R_3$ and $R_4$ are as defined for (I), by reaction with an acid chloride of the formula $R_2COCl$ or, respectively, an isocyanate of the formula $R_2$—N=C=O, in which $R_2$ is as defined for (I), * or with a diphenylphosphoryl azide derivative in a basic medium, followed by an acid treatment, to give the intermediate amine of the formula

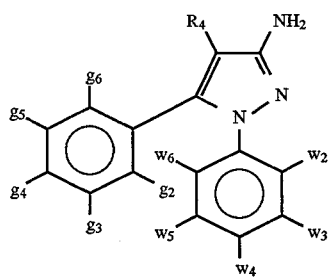

in which $w_2$, $w_3$, $w_4$, $w_5$ and $w_6$, $g_2$, $g_3$, $g_4$, $g_5$ and $g_6$ and $R_4$ are as defined for (I), which is reacted with an acid chloride $R_2COCl$ or an isocyanate $R_2$—N=C=O to give respectively the amides and ureas of the formulae

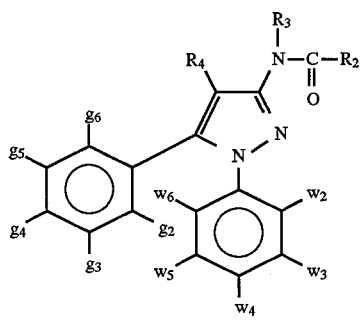

and

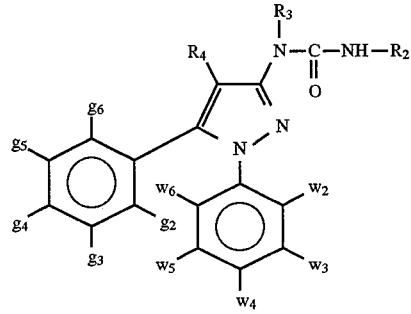

in which $w_2$, $w_3$, $w_4$, $w_5$ and $w_6$, $g_2$, $g_3$, $g_4$, $g_5$ and $g_6$ and $R_4$ are as defined for (I) and $R_3$ is hydrogen, the same compounds in which $R_3$ is other than hydrogen being prepared from the above primary amine (VII) converted to a secondary amine of the formula

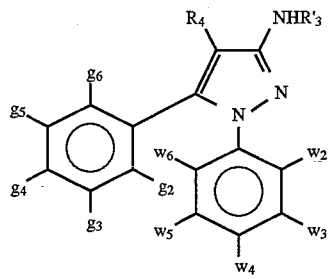

in which $w_2$, $w_3$, $w_4$, $w_5$ and $w_6$, $g_2$, $g_3$, $g_4$, $g_5$ and $g_6$ and $R_4$ are as defined for (I) and $R'_3$ is ($C_1$–$C_2$)-alkyl, which are then reacted with an acid chloride $R_2COCl$ or an isocyanate $R_2$—N=C=O to give the amides and ureas of formulae (Id) and (Ie) as defined above in which $R_3$ is other than hydrogen, * or with an organomanganous reagent $R_5MnX_1$, in which $R_5$ is as defined for (I) and $X_1$ is a halogen, to give the ketone derivatives of the formula

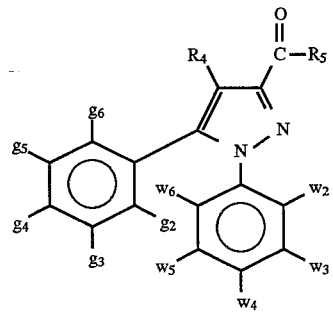

the resulting compounds then being converted to one of their salts, where appropriate.

In a preferential procedure, the pyrazoles of formula (I) can be synthesized from the corresponding esters by conversion of the ester group to an amide, urea or ketone via the acid and the acid chloride.

Said esters are synthesized by applying the method described in Berichte, 1887, 20, 2185.

The reaction scheme for the preparation of the compounds (I) via their methyl or ethyl esters (Alk=$CH_3$ or $C_2H_5$) is represented by SCHEME 1 below:

SCHEME 1

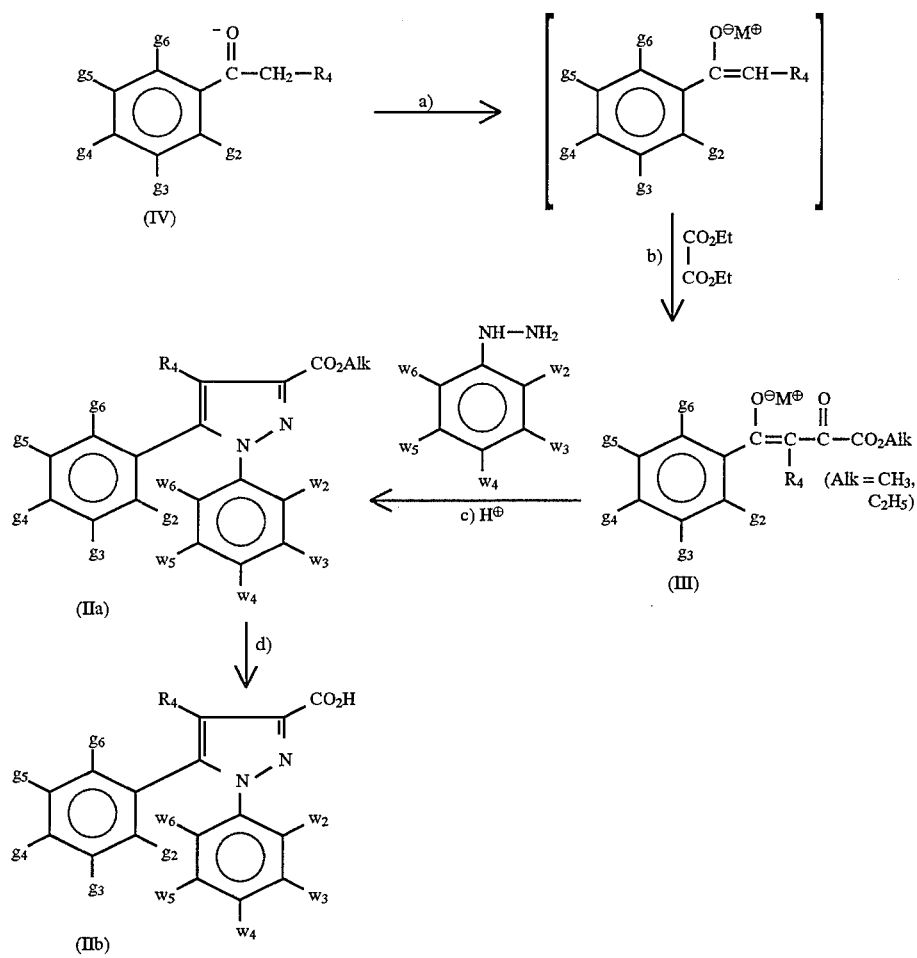

The first step a) consists in preparing an alkali metal salt of an acetophenone derivative of formula (IV), in which $R_4$ and $g_2$, $g_3$, $g_4$, $g_5$ and $g_6$ are as defined above for (I), to which an equimolar amount of diethyl oxalate is then added (step b) to give the ketoester of formula (III).

In the case where $R_4$=H, the alkali metal will preferably be sodium and the salt of the ketoester (III) (Alk=$CH_3$) will be obtained according to Bull. Soc. Chim. Fr., 1947, 14, 1098, using sodium methylate in methanol to perform step a).

In the case where $R_4$=$CH_3$, the alkali metal will preferably be lithium and the salt of the ketoester (III) (Alk=$C_2H_5$) will be obtained according to J. Heterocyclic Chem. 1989, 26, 1389, using the lithium salt of hexamethyldisilazane in ethyl ether to perform step a).

The alkali metal salts (III) prepared in this way are then refluxed in acetic acid with an excess of a hydrazine derivative (step c). Precipitation in iced water gives the 3-pyrazole esters (IIa).

These esters (IIa) are then converted to their acids (IIb) by reaction with an alkaline agent, for example potassium hydroxide, followed by acidification (step d).

In SCHEME 1 above, the esters of formula (IIa) in which $w_2$ and $w_4$ are a chlorine atom, $w_3$, $w_5$ and $w_6$ are hydrogen, $g_4$ is a chlorine atom, $g_2$, $g_3$, $g_5$ and $g_6$ are hydrogen and Alk is a $(C_1-C_5)$-alkyl, and the corresponding acids (IIb), are novel key intermediates for the preparation of the particularly advantageous compounds (i) and therefore represent a further feature of the invention; these compounds have formula (II'a) or (II'b):

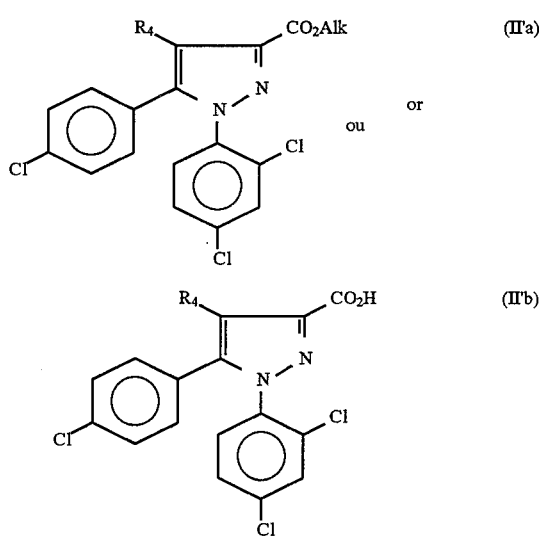

When X is a direct bond, the amides according the invention of formula (Ia):

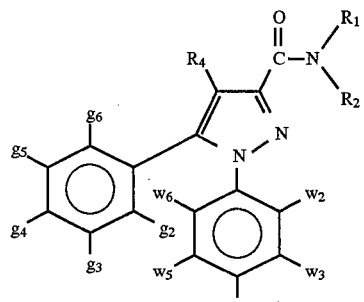

(Ia, where X = direct bond)

in which $w_2$, $w_3$, $w_4$, $w_5$ and $w_6$, $g_2$, $g_3$, $g_4$, $g_5$ and $g_6$ and $R_1$, $R_2$ and $R_4$ are as defined for (I), are prepared from a functional derivative of the acids (IIb), preferably a chloride, by the usual methods so that said acids (IIb) can be substituted by an amine of the formula $HNR_1R_2$, prepared by the usual methods, to give the compounds (Ia) according to the invention.

For example, when it is desired to prepare a compound of formula (Ia) in which $g_2$, $g_3$, $g_5$, $g_6$, $w_3$, $w_5$ and $w_6$ are hydrogen, $g_4$, $w_2$ and $w_4$ are a chlorine atom, $R_4$ is methyl, $R_1$ is hydrogen and $R_2$ is 1-piperidinyl (namely N-piperidino-5-(4-chlorophenyl)-1(2,4-dichlorophenyl)-4-methyl-pyrazole-3-carboxamide), a functional derivative of 5-(4-chlorophenyl)-1-(2,4-dichlorophenyl)-4-methyl-pyrazole-3-carboxylic acid (a compound of formula (II'b) in which $R_4$ is methyl) is reacted with 1-aminopiperidine in an organic solvent in the presence of a base. The acid chloride, the anhydride, the mixed anhydride, a straight or branched $C_1$–$C_4$ alkyl ester, an activated ester such as p-nitrophenyl ester, or the free acid appropriately activated, for example by N,N-dicyclohexylcarbodiimide or benzotriazol-N-oxotris (dimethylamino)phosphonium hexafluorophosphate (BOP) can be used as the functional derivative of the acid.

Thus, 5-(4-chlorophenyl)-1-(2,4-dichlorophenyl-4-methyl-pyrazole-3-carboxylic acid chloride, obtained by reaction of thionyle chloride with 5-(4-chlorophenyl)-1-(2, 4-dichlorophenyl)-4-methyl-pyrazole-3-carboxylic acid, can be reacted with 1-aminopiperidine in a solvent such as dichloromethane in an inert atmosphere, at a temperature between 0° C. and room temperature, in the presence of a base such as triethylamine.

Alternately, the mixed anhydride of 5-(4-chlorophenyl)-1-(2,4-dichlorophenyl)-4-methyl-pyrazole-3-carboxylic acid can be prepared by reaction of ethylchloroformate with the said acid in the presence of a base such as triethylamine, and then reacted with 1-aminopiperidine in a solvent such as dichloromethane in an inert atmosphere, at a temperature between 0° C. and room temperature, in the presence of a base such as triethylamine.

When X is a group $—(CH_2)_xN(R_3)—$, in which x and $R_3$ are as defined for (I), the amides and the ureas according to the invention of formulae (Ib) and (Ic):

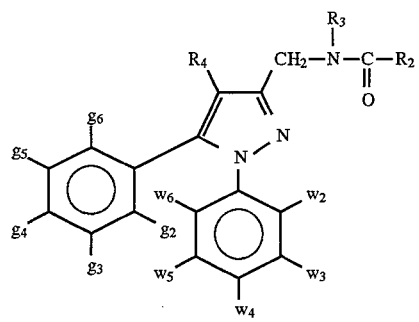

(Ib, where x = 1 and R = $R_2$)

and

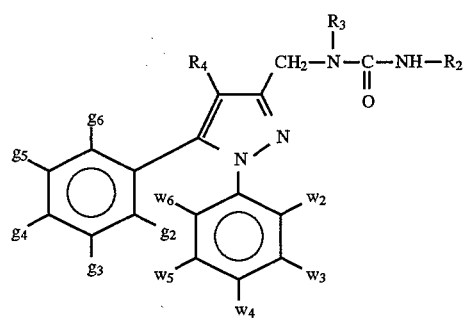

(Ic, where x = 1 and R = $NHR_2$)

in which $w_2$, $w_3$, $w_4$, $w_5$ and $w_6$, $g_2$, $g_3$, $g_4$, $g_5$ and $g_6$ and $R_2$, $R_3$ and $R_4$ are as defined for (I), are prepared from the above-described ester (IIa) according to SCHEME 2 below:

SCHEME 2

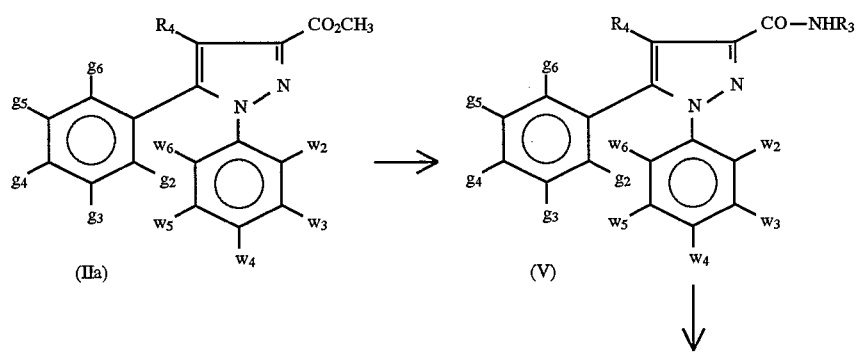

SCHEME 2 -continued

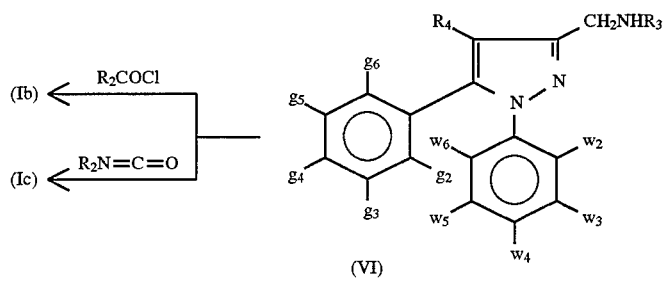

The conversion of the ester (IIa) to the intermediate amide (V) can be effected for example via the corresponding acid chloride, the latter being reacted with an amine $R_3NH_2$ in an alkanol such as ethanol.

The reduction of the amide (V) to the amine (VI) is then effected by means of a metal hydride such as lithium aluminum hydride or, preferably, by means of the complex $BH_3$-THF in solution in THF under reflux. The amine (VI) is then converted to the amide (Ib) or the urea (Ic) according to the invention by the conventional methods, for example by reaction with an acid chloride $R_2COCl$ or an isocyanate $R_2-N=C=O$, respectively.

The amides and the ureas according to the invention of formulae (Id) and (Ie):

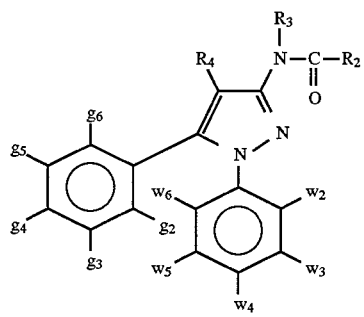

(Id, where $X = -N(R_3)-$)

and

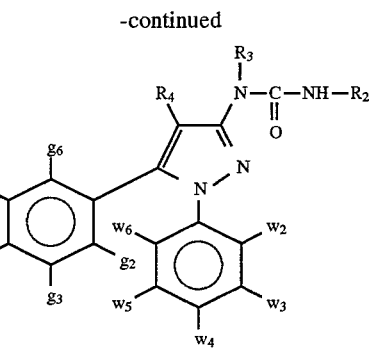

(Ie, where $X = -N(R_3)-$ and $R_1 = H$)

in which $g_2$, $g_3$, $g_4$, $g_5$ and $g_6$, $w_2$, $w_3$, $w_4$, $w_5$ and $w_6$ and $R_2$, $R_3$ and $R_4$ are as defined for (I), are prepared from the previously obtained pyrazole-3-carboxylic acids according to SCHEME 3 below:

SCHEME 3

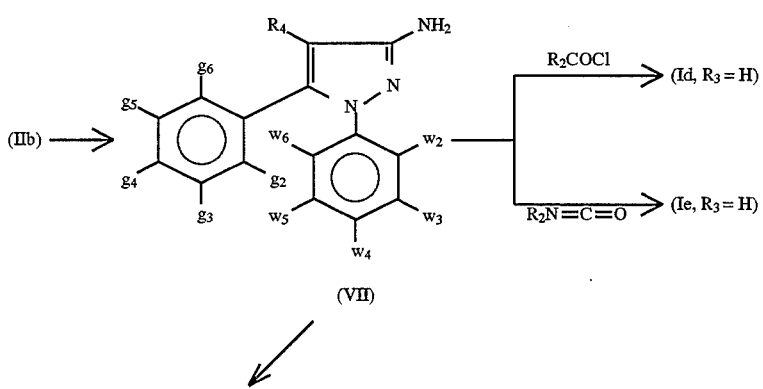

-continued
SCHEME 3

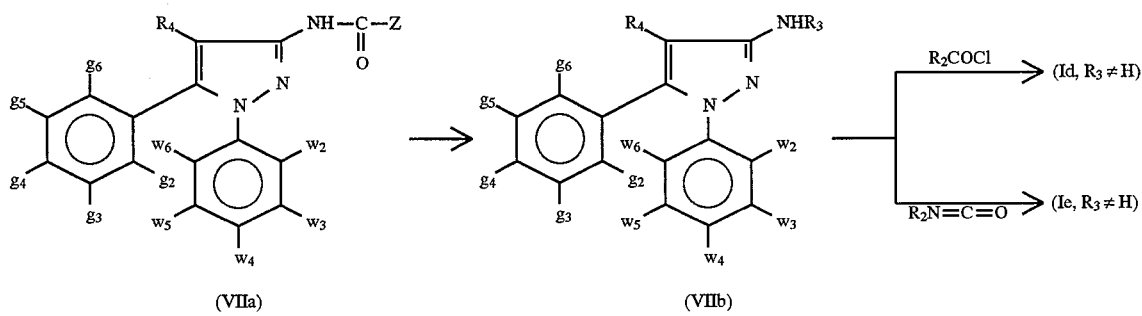

The acids (IIb) are converted to the corresponding amines (VII) by means of a Curtius reaction, for example using diphenylphosphoryl azide in a basic medium, followed by a treatment with a strong acid such as hydrochloric acid or trifluoroacetic acid, as described in Synthesis, 1990, 295. The amines (VII) are then converted to the amides (Id) or ureas (Ie) according to the invention by the usual methods, for example by reaction with an acid chloride $R_2COCl$ in the case of (Id) where $R_3$=H, or with an isocyanate $R_2$—N=C=O in the case of (Ie) where $R_3$=H.

Alternatively, the ureas (Ie) where $R_3$=H can be prepared by the reverse reaction: the acids (IIb) are converted to corresponding isocyanates (VIIc) as described in J. Org. Chem. 1961, 26, 3511, according to SCHEME 4 below.

Reaction of the isocyanates (VIIc) with an amine $R_2NH_2$ then gives the ureas (Ie) directly.

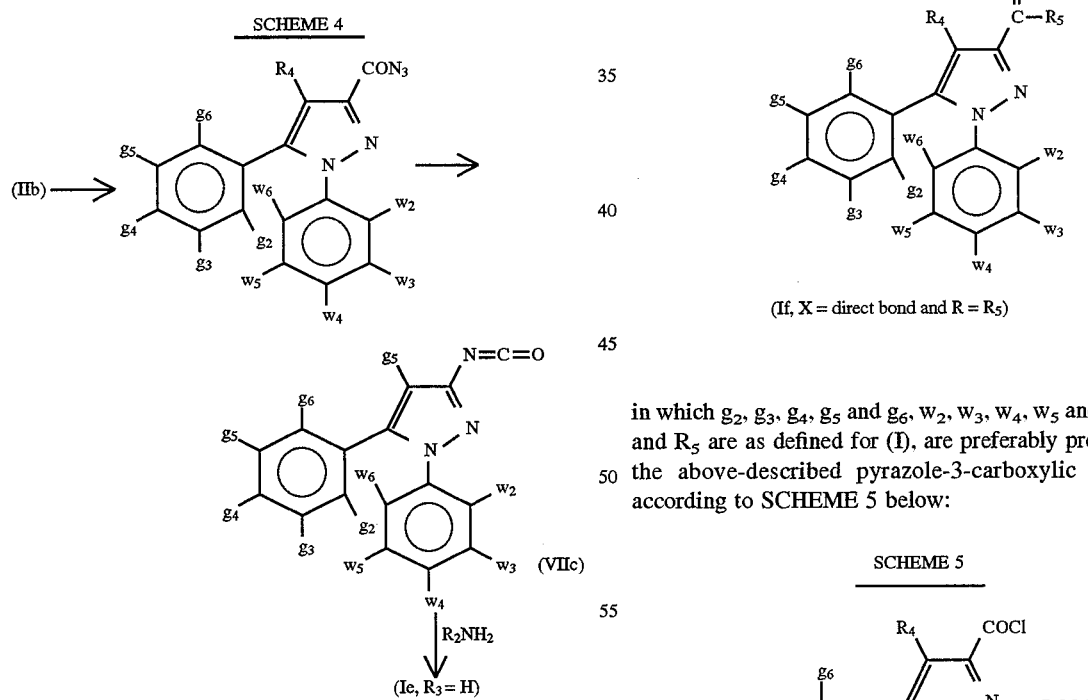

To prepare the compounds (Id) and (Ie) in which $R_3$ is other than hydrogen, the primary amines (VII) are first converted to secondary amines (VIIb) by a reaction sequence such as reaction with an acid chloride $R'_3COCl$ (where $R'_3$=($C_1$–$C_2$) alkyl), followed by reduction of the amide (VIIa) obtained, for example by reaction with $BH_3$ in THF. In the case where $R_3$ is a methyl, it is preferable to react the amines (VII) with tert-butyl dicarbonate, $(BOC)_2O$, or with a mixture of formic acid and acetic anhydride, giving respectively the carbamate (VIIa, Z=OtBu) or the formamide (VIIa, Z=H), which products are then reduced, for example with $LiAlH_4$, to give the amines (VIIb, $R_3$=$CH_3$).

The secondary amines (VIIb) are then converted to the amides (Id) or ureas (Ie) according to the invention as described above.

The ketone derivatives according to the invention of formula (If):

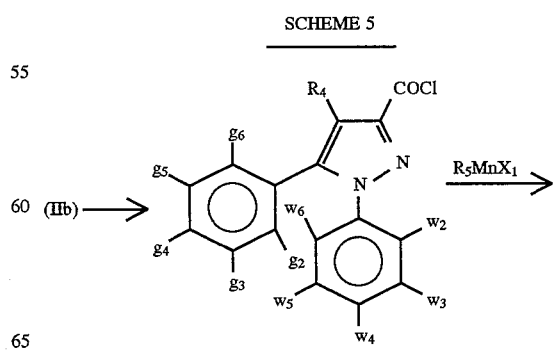

(If, X = direct bond and R = $R_5$)

in which $g_2$, $g_3$, $g_4$, $g_5$ and $g_6$, $w_2$, $w_3$, $w_4$, $w_5$ and $w_6$ and $R_4$ and $R_5$ are as defined for (I), are preferably prepared from the above-described pyrazole-3-carboxylic acids (IIb) according to SCHEME 5 below:

SCHEME 5

-continued
SCHEME 5

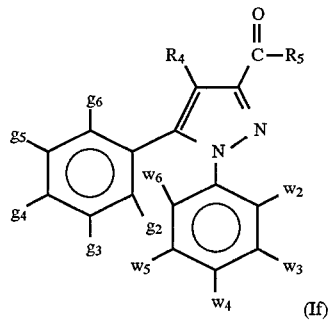

The acids (IIb) are converted to the acid chlorides by the conventional methods; the latter are then converted to the ketone derivatives (If) according to the invention by reaction with an appropriate organomanganous reagent $R_5MnX_1$, in which $R_5$ is as defined for (I) and $X_1$ is a halogen, preferably a chlorine atom, for example using the method described in Tetrahedron Letters, 1989, 30, 7369.

Alternatively, the ketone derivatives (If) can be prepared from the acids (IIb) via the nitriles (IIc) according to SCHEME 6 below:

SCHEME 6

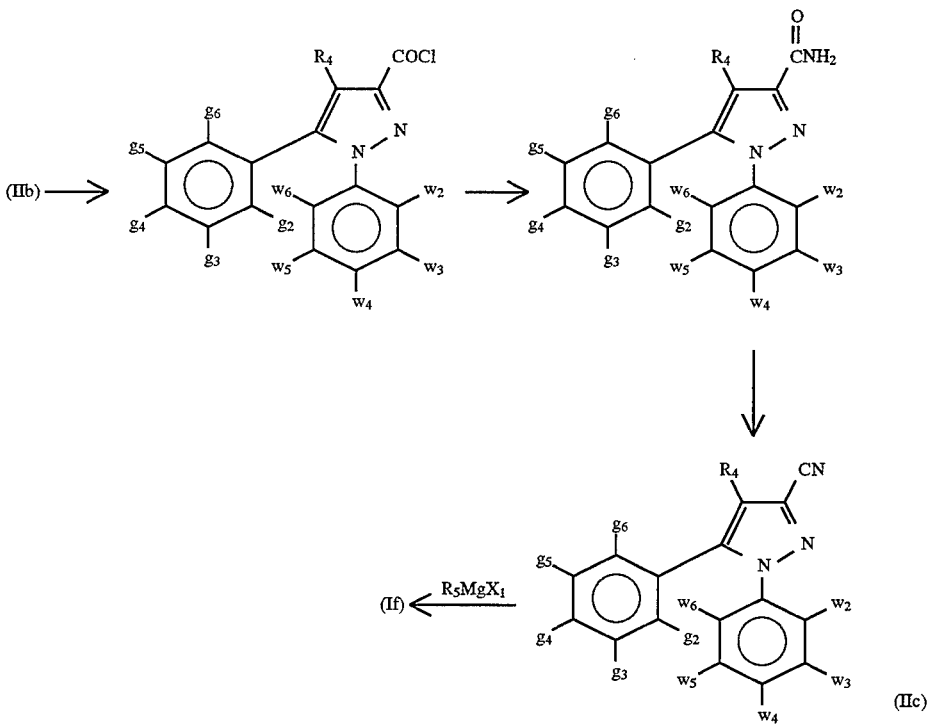

(IIb) is converted to (IIc) by a conventional method such as, for example, conversion to the acid chloride followed by amination ($NH_3$/THF/water) and dehydration of the amide obtained, for example by treatment with $CH_3SO_2Cl$ in pyridine as described in J. Am. Chem. Soc., 1955, 77, 1701.

The nitriles (IIc) obtained in this way are then treated with organometallic reagents, preferably organomagnesium reagents of the formula $R_5MgX_1$, to give the ketone derivatives (If) after acid treatment.

The compounds of formula (I) obtained in this way are isolated, in the form of the free base or, where appropriate, a salt or a solvate, by the conventional techniques.

When the compound of formula (I) is obtained in the form of the free base, a salt is formed by treatment with the chosen acid in an organic solvent. Treatment of the free base, for example dissolved in an alcohol such as isopropanol, an ether such as diethylether or in acetone, with a solution of the chosen acid in the same solvent gives the corresponding salt, which is isolated by the conventional techniques. The hydrochloride, hydrobromide, sulfate, hydrogensulfate, dihydrogenphosphate, methanesulfonate, oxalate, maleate, fumarate, naphthalene-2-sulfonate and paratoluenesulfonate, for example, are prepared in this way.

When the reaction is complete, the compounds of formula (I) can be isolated in the form of one of their salts, where appropriate, for example the hydrochloride or the oxalate; in this case, if necessary, the free base can be prepared by neutralizing said salt with a mineral or organic base such as sodium or ammonium hydroxide or triethylamine, or with an alkali metal carbonate or bicarbonate such as sodium or potassium carbonate or bicarbonate, and converted into another salt such as the methanesulfonate, fumarate or naphtalene-2-sulfonate.

The acid (II'b) in which $R_4$ is methyl, namely 5-(4-chlorophenyl)-1-(2,4-dichlorophenyl)-4-methylpyrazole-3-carboxylic acid can for example be prepared as illustrated below in route 1 or route 2:

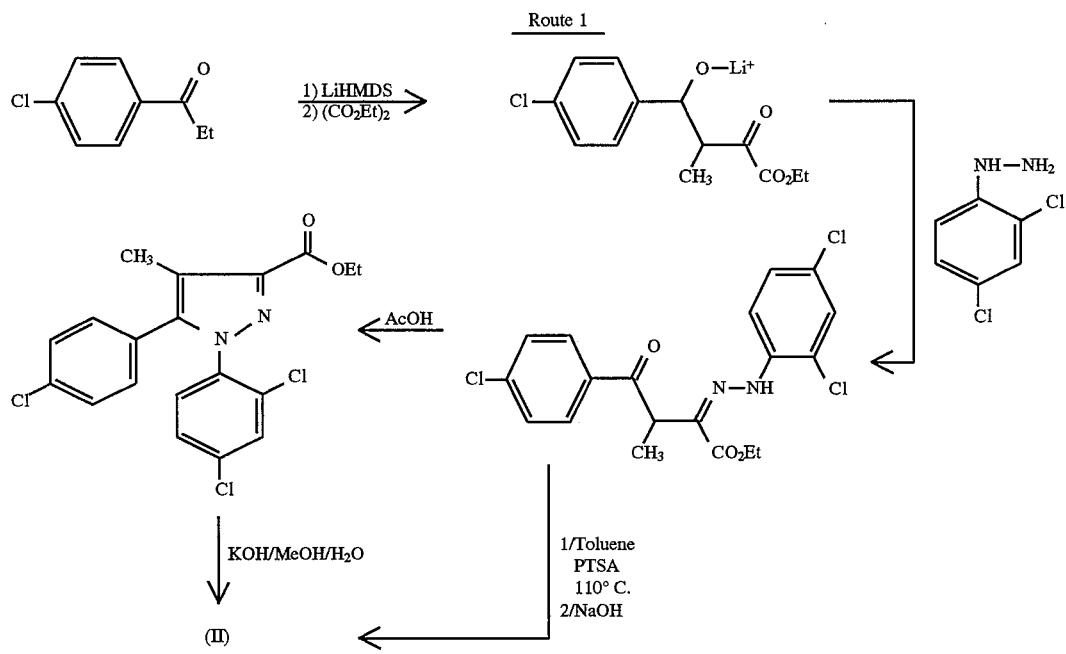
LiHMDS: lithium salt of hexamethyldisilazane
PTSA: paratoluenesulfonic acid.
The first step is carried out according to J. Heterocyclic Chem., 1989, 26, 1389.
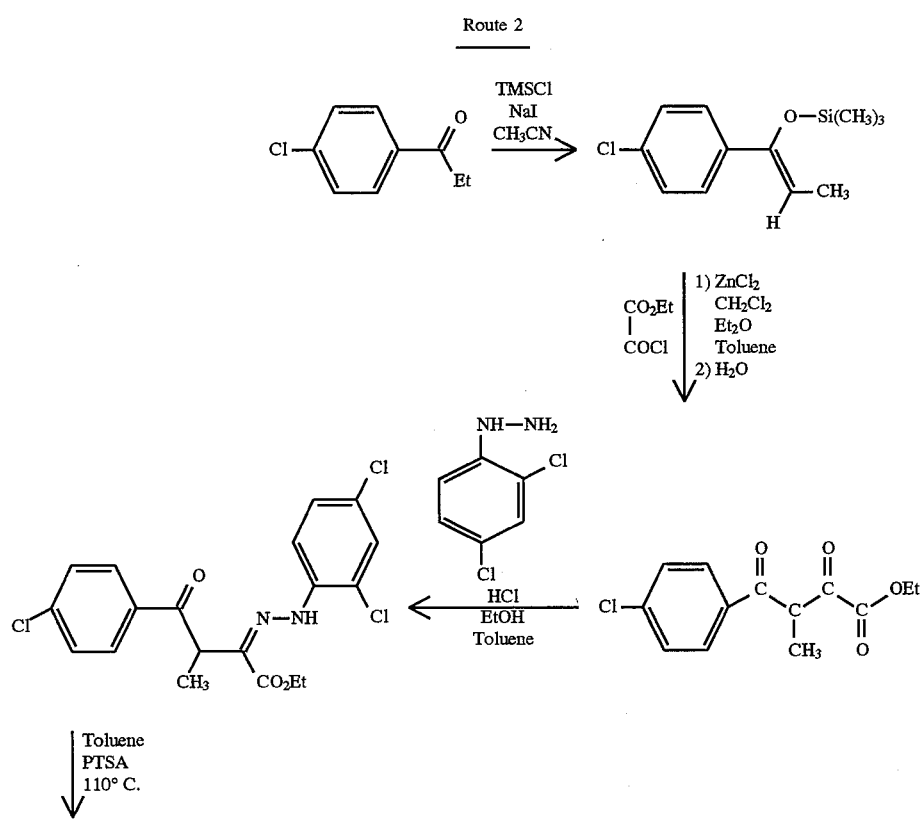

-continued
Route 2

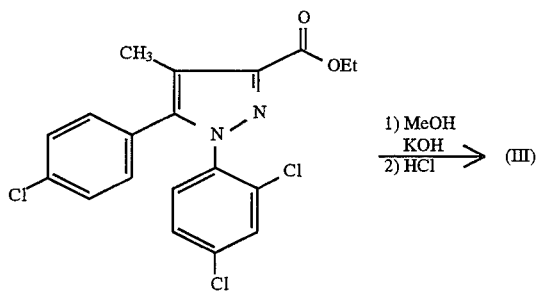

1) MeOH
   KOH
2) HCl  →  (III)

TMSCl: chlorotrimethylsilane
PTSA: paratoluenesulfonic acid

The first step is carried out according to the method described by E. S. Schweizer in J. Org. Chem., 1987, 52, 1324–1332. The second step is carried out according to the method described by R. E. Tirpak et al. in J. Org. Chem., 1982, 47, 5099–5102.

The amines of formula $HNR_1R_2$ are either commercially available, or described in the literature, or prepared by known methods according to the PREPARATIONS described below.

Preferred examples of these amines are those mentioned below:

(1) bicyclo[3.2.1]octan-2-ylamine prepared according to H. Maskill et al., J. Chem. Soc. Perkin II, 1984, 119;

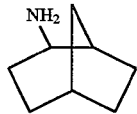

(2) bicyclo[2.2.2]octan-2-ylamine prepared according to R. Seka et al., Ber. 1942, 1379;

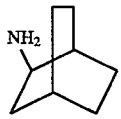

(3) endo- and exo-bicyclo[3.2.1]octan-3-ylamine prepared according to H. Maskill et al., J. Chem. Soc. Perkin Trans. II, 1984, 1369;

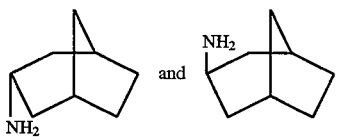

(4) endo- and exo-7-oxabicyclo[2.2.1]heptan-2-ylamine prepared according to W. L. Nelson et al., J. Heterocyclic Chem., 1972, 9, 561;

(5) endo-tricyclo[5.2.1.0$^{2,6}$]decan-8-amine prepared according to G. Buchbauer et al., Arch. Pharm., 1990, 323, 367;

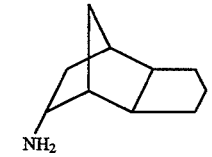

(6) endo-1,3,3-trimethylbicyclo[2.2.1]heptan-2-ylamine prepared according to Ingersoll et al., J. Am. Chem. Soc., 1951, 73, 3360;

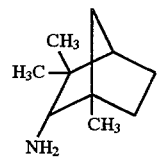

(7) 3-methylcyclohexylamine prepared according to Smith et al., J. Org. Chem., 1952, 17, 294;

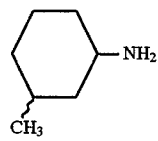

(8) 2,6-dimethylcyclohexylamine prepared according to Cornubert et al., Bull. Soc. Chim. Fr., 945, 12, 367;

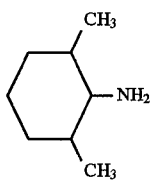

(9) 2-methoxycyclohexylamine prepared according to Noyce et al., J. Am. Chem. Soc., 1954, 76, 768;

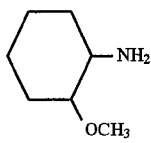

(10) 4-ethylcyclohexylamine prepared according to A. Shirahata et al., Biochem. Pharmacol., 1991, 41, 205;

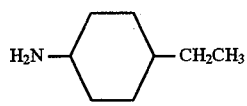

(11) bicyclo[2.2.21]oct-2-en-5-amine prepared according to H. L. Goering et al., J. Am. Chem. Soc., 1961, 83, 1391;

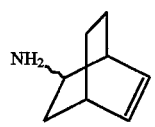

(12) N-ethyl-1-adamantylamine prepared according to V. L. Narayanan et al., J. Med. Chem., 72, 15, 443;

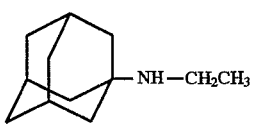

(13) tricyclo[2.2.1.0$^{2,6}$]heptan-3-ylamine prepared according to G. Muller et al., Chem. Ber., 65, 98, 1097;

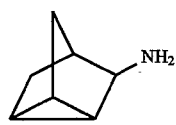

(14) N-methyl-exo-bicyclo[2.2.1]heptan-2-ylamine prepared according to W. G. Kabalka et al., Synth. Commun., 1991, 20, 231;

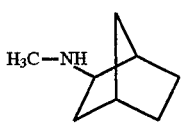

(15) 2-azabicyclo[2.2.1]heptan-2-yl-amine prepared according to J. Am. Chem. Soc. 1982, 104, 5292, starting from 2-azabicyclo[2.2.1]heptane prepared according to Chem. Ber., 1983, 116, 1081.

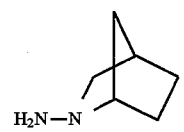

(16) 2-azabicyclo [2.2.2]octan-2-yl-amine prepared according to J. Am. Chem. Soc. 1982, 104, 5292.

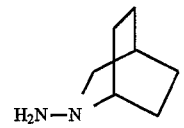

The amines $R_3NH_2$ are commercially available or are prepared by known methods.

The acid chlorides $R_2COCl$ are commercially available or are prepared from the corresponding acids by known methods.

The isocyanates $R_2$—N=C=O are also commercially available or are prepared from the corresponding amines (reaction with phosgene) or corresponding acids (Curtius rearrangement) by known methods.

The compounds according to the invention were subjected to biochemical tests.

The compounds (I) and their salts, where appropriate, exhibited a good affinity in vitro for the cannabinoid receptors in tests performed under the experimental conditions described by Devane et al., Molecular Pharmacology, 1988, 34, 605–613.

The compounds according to the invention also possess an affinity for the cannabinoid receptors present on preparations of electrically stimulated, isolated organs. These tests were performed on the guinea-pig ileum and on the mouse vas deferens according to Roselt et al., Acta Physiologica Scandinavia, 1975, 94, 142–144, and according to Nicolau et al., Arch. Int. Pharmacodyn., 1978, 236, 131–136.

In particular, the compound of formula (I) in which $g_2$, $g_3$, $g_5$, $g_6$, $w_3$, $w_5$ and $w_6$ are hydrogen, $w_2$ and $w_4$ are a chlorine atom, $R_4$ is methyl, X is a direct bond and R is 1-piperidinylamino (namely N-piperidino-5-(4-chlorophenyl)-1-(2,4-dichlorophenyl)-4-methyl-pyrazole-3-carboxamide), or one of its pharmaceutically acceptable salts, exhibits a very good affinity for the central cannabinoid receptors. This compound is a potent and selective antagonist of the central cannabinoid receptors and has a Ki of about 2 nM. It is from 500 to 1000 times more active on the central receptor as on the peripheral receptor; it is also active upon oral administration and penetrates the blood-brain barrier. The good penetration of this compound in the central nervous system as well as its antagonist character are confirmed by the results obtained with the model of the antagonism of hypothermia induced by an agonist of cannabinoid receptors. Especially, this compound antagonizes the hypothermia induced by WIN 55 212-2 in mice with an $ED_{50}$ of 0.3 mg/kg i.p. and 0.4 mg/kg per os. In this test (Pertwee R. G., 1985:263–277; in Marijuana 84, Ed. Harvey, D. Y., IRL Press, Oxford), the above compound exerted its action for 8 to 10 hours after oral administration of a dose of 3 mg/kg.

In addition, the above compound, upon subcutaneous administration, improves the memory capacities of rats in the test of the central memory (A Pério et al. in Psychopharmacology, 1989, 97, 262–268).

The compounds according to the invention are generally administered in dosage units.

Said dosage units are preferably formulated in pharmaceutical compositions in which the active principle is mixed with a pharmaceutical excipient.

Thus, according to another of its features, the present invention relates to pharmaceutical compositions in which a compound of formula (I) or one of its pharmaceutically acceptable salts is present as the active principle.

The compounds of formula (I) above and their pharmaceutically acceptable salts can be used in daily doses of 0.01 to 100 mg per kilogram of body weight of the mammal to be treated, preferably in daily doses of 0.1 to 50 mg/kg. In humans, the dose can preferably vary from 0.5 to 4000 mg per day, more particularly from 2.0 to 1000 mg, depending on the age of the subject to be treated or the type of treatment: prophylactic or curative.

In the pharmaceutical compositions of the present invention for oral, sublingual, subcutaneous, intramuscular, intravenous, transdermal, local or rectal administration, the active principles can be administered to animals and humans in unit forms of administration, mixed with conventional pharmaceutical carriers. The appropriate unit forms of administration include forms for oral administration, such as tablets, gelatin capsules, powders, granules and solutions or suspensions to be taken orally, forms for sublingual and buccal administration, aerosols, implants, forms for subcutaneous, intramuscular, intravenous, intranasal or intraocular administration and forms for rectal administration.

In the pharmaceutical compositions of the present invention, the active principle is generally formulated as dosage units containing from 0.5 to 1000 mg, preferably from 1 to 500 mg, more preferably from 2 to 200 mg of said active principle per dosage unit for daily administrations.

When preparing a solid composition in the form of tablets, a wetting agent such as sodium laurylsulfate can be added to the active principle optionally micronized, which is then mixed with a pharmaceutical vehicle such as silica, gelatin, starch, lactose, magnesium stearate, talc, gum arabic or the like. The tablets can be coated with sucrose, with various polymers or other appropriate substances or else they can be treated so as to have a prolonged or delayed activity and so as to release a predetermined amount of active principle continuously.

A preparation in the form of gelatin capsules is obtained by mixing the active principle with a diluent such as a glycol or a glycerol ester and pouring the mixture obtained into soft or hard gelatin capsules.

A preparation in the form of a syrup or elixir can contain the active principle together with a sweetener, which is preferably calorie-free, methyl-paraben and propylparaben as an antiseptic, a flavoring and an appropriate color.

The water-dispersible powders or granules can contain the active principle mixed with dispersants or wetting agents, or suspending agents such as polyvinyl-pyrrolidone, and also with sweeteners or taste correctors.

Rectal administration is effected using suppositories prepared with binders which melt at the rectal temperature, for example cacao butter or polyethylene glycols.

Parenteral, intranasal or intraocular administration is effected using aqueous suspensions, isotonic saline solutions or sterile and injectable solutions which contain pharmacologically compatible dispersants and/or wetting agents, for example propylene glycol, butylene glycol, or polyethylene glycol.

Thus a cosolvent, for example an alcohol such as ethanol or a glycol such as polyethylene glycol or propylene glycol, and a hydrophilic surfactant such as Tween® 80, can be used to prepare an aqueous solution injectable by intravenous route. The active principle can be solubilized by a triglyceride or a glycerol ester to prepare an oily solution injectable by intramuscular route.

Transdermal administration is effected using multilaminated patches or reservoirs into which the active principle is in the form of an alcoholic solution.

Administration by inhalation is effected using an aerosol containing for example sorbitan trioleate or oleic acid together with trichlorofluoromethane, dichlorotetrafluoroethane or any other biologically compatible propellant gas.

The active principle can also be formulated as microcapsules or microspheres, optionally with one or more carriers or additives.

Among the prolonged-release forms which are useful in the case of chronic treatments, implants can be used. These can be prepared in the form of an oily suspension or in the form of a suspension of microspheres in an isotonic medium.

The active principle can also be presented in the form of a complex with a cyclodextrin, for example $\alpha$-, $\beta$- or $\gamma$-cyclodextrin, 2-hydroxypropyl-$\beta$-cyclodextrin or methyl-$\beta$-cyclodextrin.

The compounds of formula (I) formulated in this way can be used for the treatment of immunomodulation, migraine, asthma, epilepsy, glaucoma, Parkinson's disease, dyskinesia, neuropathy, memory and thymic disorders, vomiting, ischemia, angor, orthostatic hypotension, cardiac insufficiency, stress, anxio-depressive disorders or psychosomatic-induced disorders.

Especially, the compound of formula (Ia) in which $g_2$, $g_3$, $g_5$, $g_6$, $w_3$, $w_5$ and $w_6$ are hydrogen, $g_4$, $w_2$ and $w_4$ are a chlorine atom, $R_4$ is methyl, $R_1$ is hydrogen and $R_2$ is 1-piperidinyl (namely N-piperidino-5-(4-chlorophenyl)-1-(2,4-dichlorophenyl)-4-methyl-pyrazole-3-carboxamide), as such or optionally in the form of a pharmaceutically acceptable salt or a solvate, can be used as the active principle of drugs intended for the treatment of the diseases of the central nervous system in mammals, thanks to its remarkable properties, especially its high affinity, its selectivity towards the central receptor as well as its capacity to penetrate the blood-brain barrier.

The toxicity of the above compound is compatible with its use as a psychotropic drug, especially for the treatment of thymic disorders, anxiety disorders, mood disorders, vomiting, memory disorders, cognitive disorders, neuropathies, migraine, stress, psychosomatic-induced diseases, epilepsy, dyskinesia or Parkinson's disease.

The above compound can also be used as a drug for the treatment of appetite disorders, especially as an anorexic, for the treatment of schizophrenia, delirious disorders, psychotic disorders in general as well as for the treatment of disorders associated with the use of psychotic substances. Furthermore, the above compound can be used in cancer chemotherapy.

The use of the above compound as a drug for the treatment of appetite disorders, anxiety disorders, mood disorders, schizophrenia, psychotic disorders, memory disorders, cognitive disorders and dyskinesia, as well as its use in cancer chemotherapy, constitute a further feature of the present invention.

The following Examples illustrate the invention without however implying a limitation.

The melting or decomposition points of the products, m.p., were measured in a capillary tube with a Tottoli apparatus; in some cases, differential scanning calorimetry (DSC) was used to measure the melting temperature.

The following abbreviations are used in the preparations and in the examples:

THF: tetrahydrofuran
Et$_2$O or ether: diethyl ether
iPr$_2$O or iso ether: diisopropyl ether
EtOH: ethanol
AcOEt: ethyl acetate
MeOH: methanol
DCM: dichloromethane
KOH: potassium hydroxide
AcOH: acetic acid
HCl: hydrochloric acid
NaCl: sodium chloride
RT: room temperature
DSC: differential scanning calorimetry
M.p.: melting point
CH$_2$Cl$_2$: dichloromethane
Na$_2$CO$_3$: sodium carbonate
MgSO$_4$: magnesium sulfate The following abbreviations are used in the interpretation of the NMR spectra:
s: singlet
d: doublet
t: triplet
q: quadruplet
m: unresolved signals or multiplet.

The enantiomeric excess of the optically active amines, e.e., was determined by $^{19}$F NMR after reaction with the chloride of S(+) Mosher's acid according to J. Org. Chem., 1969, 34, 2543.

The optical rotations, $[\alpha]_D^{20}$, were measured at c=1 in ethanol.

PREPARATIONS

A. AMINES NHR$_1$R$_2$ 1. (1R,2S-endo)-(+)-Bicyclo[2.2.1]heptan-2-yl-amine (1R,2S-endo)-(−)-Bicyclo[2.2.1]heptane-2-carboxylic acid is prepared according to Tetrahedron Letters, 1985, 26, 3095.

By means of a Curtius reaction carried out according to J. Org. Chem., 1961, 26, 3511, this is then converted to the corresponding (1R, 2S-endo)-(+)-amine.

$[\alpha]_D^{20}$ 32 +13.4° (c=1, EtOH).

e.e.>95%, δ(CF$_3$)=6.67 ppm relative to CF$_3$CO$_2$H.

2. (1R,2R-exo)-(−)-Bicyclo[2.2.1]heptan-2-yl-amine

The (1R,2S-endo)-(−)-bicyclo[2.2.1]heptane-2-carboxylic acid prepared in the previous Example is converted to its (1R,2R-exo)-(−) isomer according to J. Am. Chem. Soc., 1983, 105, 950, and then converted to the corresponding (1R,2R-exo)-(−)-amine as described in the previous Example.

$[\alpha]_D^{20}$=−17.7° (c=1, EtOH).

e.e.>94% (determined as above, δ(CF$_3$)=6.81 ppm).

3. (1S,2R-endo)-(−)-Bicyclo[2.2.1]heptan-2-ylamine (1S,2R-endo)-(+)-Bicyclo[2.2.1]heptane-2-carboxylic acid is prepared according to Tetrahedron Letters, 1989, 30, 5595, and then converted to the corresponding (1S,2R-endo)-(−)-amine as described above.

e.e.>95% (determined as above, δ(CF$_3$)=6.62 ppm).

4. (1S,2S-exo)-(+)-Bicyclo[2.2.1]heptan-2-ylamine

The (1S,2R-endo)-(+)-acid prepared in the previous Example is converted to its (1S,2S-exo)-(+) isomer according to according to J. Am. Chem. Soc., 83, 105, 950, and this is then converted to the corresponding (1S,2S-exo)-(+)-amine as described above.

e.e.>94% (determined as above, δ(CF$_3$)=6.91 ppm).

5. exo-3-Chlorobicyclo[3.2.1]oct-3-enyl-2-amine 0.4 g of PtO$_2$ is added to a solution of 6.1 g of exo-3-chloro-2-azidobicyclo[3.2.1]oct-3-ene, obtained according to J. Chem. Soc. Perkin Trans. II, 1984, 119, in 600 ml of ethanol and 60 ml of CHCl$_3$ and hydrogenation is carried out in a Parr apparatus at 4 bar and room temperature until the azide group has disappeared. After filtration on Célite, the reaction mixture is evaporated and the residue is crystallized from an ethanol/CHCl$_3$ mixture to give 0.49 g of the hydrochloride of the expected amine.

M.p.>240° C.

6. N-Ethyl-exo-bicyclo[2.2.1]heptan-2-ylamine 6.1. N-Acetyl-exo-bicyclo[2.2.1]heptan-2-ylamine A solution of 3.50 ml of acetyl chloride in 10 ml of CH$_2$Cl$_2$ is added dropwise to a solution of 5.00 g of exo-bicyclo[2.2.1]heptan-2-ylamine and 6.90 ml of triethylamine in 50 ml of CH$_2$Cl$_2$, cooled to 0° C. After stirring for 16 hours at room temperature, the mixture is poured into 100 ml of iced water and the organic phase is separated off and washed with a 5% solution of HCl, then with water and then with a saturated solution of NaCl. After drying over MgSO$_4$ and evaporation of the solvents, 5.80 g of the expected acetamide are obtained.

M.p.=128° C.

6.2. N-Ethyl-exo-bicyclo[2.2.1]heptan-2-ylamine

A solution of 5.10 g of the above derivative in 30 ml of THF is added dropwise to a suspension of 2.18 g of LiAlH$_4$ in 30 ml of THF, cooled to 0° C., and the mixture is then refluxed for 8 hours. It is hydroyzed at 0° C. with 2.2 ml of water, then 2.2 ml of a 15% solution of NaOH and then 7.5 ml of water. After stirring for 15 minutes, the precipitate is filtered off and washed with THF, the filtrate is evaporated and the residue is then taken up in 50 ml of ethyl ether. This ether solution is extracted with 5% HCl; the aqueous phase obtained is neutralized with 30% NaOH and then extracted with ethyl ether. After washing with a saturated solution of NaCl, drying over MgSO$_4$ and evaporation, 3.82 g of a pale yellow liquid are obtained. Dissolution in ethyl ether and treatment with a soluItion of gaseous HCl in anhydrous ethyl ether gives a white precipitate, which is filtered off, washed with ethyl ether and dried under vacuum to give 4.16 g of the hydrochloride of the expected amine.

M.p.=145° C. (decomposition).

7. N-(n-Propyl)-exo-bicyclo[2.2.1]heptan-2-ylamine 7.1. N-Propionyl-exo-bicyclo[2.2.1]heptan-2-ylamine This amide is obtained in the same way as the N-acetyl analog described in Example 6 above, using propionyl chloride instead of acetyl chloride.

7.2. N-(n-Propyl)-exo-bicyclo[2.2.1]heptan-2-ylamine

This amine is obtained starting from the above amide, in the same way as the N-ethyl analog described in the previous Example. Salification with HCl/Et$_2$O in an Et$_2$O/iPr$_2$O mixture gives the hydrochloride of the expected amine.

M.p.=230° C. (decomposition).

8. Bicyclo[3.3.1]nonan-9-ylamine 8.1. Bicyclo[3.3.1]nonan-9-one oxime

A solution of 1.83 g of hydroxylamine hydrochloride and 2.95 g of sodium acetate in 22 ml of water is added to a solution of 2.43 g of bicyclo[3.3.1]-nonan-9-one in 9 ml of methanol and the mixture is refluxed for 24 hours. After cooling, it is extracted with ethyl ether and the organic phases are washed with a saturated solution of NaCl, then a 5% solution of Na$_2$CO$_3$ and the water, dried over MgSO$_4$ and evaporated to give 3.00 g of oxime.

M.p.=151° C.

8.2. Bicyclo[3.3.1]nonan-9-ylamine 0.20 g of PtO$_2$ is added to a solution of 1.00 g of oxime in 250 ml of ethanol and 4 ml of CHCl$_3$ and hydrogenation is carried out in a Parr apparatus at 6 bar and room temperature for 18 hours. After filtration on Célite, the solvents are evaporated off and the residue is crystallized from an ethanol/heptane mixture to give 0.55 g of the hydrochloride of the expected amine.

M.p.>240° C.

EXAMPLE 1

N-(2-Adamantyl)-1-(2,4-dichlorophenyl)-5-(4-chlorophenyl)-1H-pyrazole-3-carboxamide

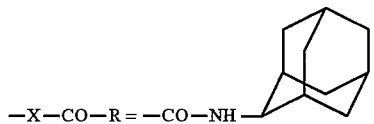

A) Sodium salt of methyl 4-chlorobenzoylpyruvate 12 g of sodium are dissolved in 250 ml of anhydrous methanol. A mixture of 64.6 ml of 4-chloroacetophenone and 67.1 ml of diethyl oxalate in 600 ml of methanol is then added, the temperature being kept below 10° C. The reaction mixture is then stirred at room temperature for 3 hours, after which 1 l of dry ether is added. Stirring is continued for 20 minutes, the mixture is filtered and the precipitate is washed with ether and dried under vacuum to give 74.6 g of the expected sodium salt.

B) Methyl 1-(2,4-dichlorophenyl)-5-(4-chlorophenyl)-1H-pyrazole-3-carboxylate A suspension of 26.3 g of the sodium salt obtained above and 23.5 g of 2,4-dichlorophenylhydrazine hydrochloride in 250 ml of acetic acid is refluxed for 4 hours. After cooling, the mixture is poured on to 250 g of ice and the crystals obtained are filtered off, washed with water and dried under vacuum to give 26.3 g of ester.

M.p.=167° C.

C) 1-(2,4-Dichlorophenyl)-5-(4-chlorophenyl)-1H-pyrazole-3-carboxylic acid

A solution of 3.70 g of KOH in 35 ml of water is added to a solution of 10.0 g of the ester obtained above in 35 ml of methanol. The mixture is refluxed for 4 hours, cooled to room temperature, poured into 100 ml of water and then neutralized with a 5% solution of HCl. The crystals obtained are filtered off, washed with water and then with pentane and dried under vacuum to give 9.50 g of acid.

M.p.=185° C.

D) 1-(2,4-Dichlorophenyl)-5-(4-chlorophenyl)-1H-pyrazole-3-carboxylic acid chloride 5.8 ml of thionyl chloride are added to a suspension of 9.50 g of the acid obtained above in 100 ml of toluene and the mixture is refluxed for 3 hours. The solvent is then evaporated off, the residue is subsequently taken up in 50 ml of toluene and the solvent is evaporated off again (procedure repeated twice) to give 8.28 g of acid chloride.

E) N-(2-Adamantyl)-1-(2,4-dichlorophenyl)-5-(4-chlorophenyl)-1H-pyrazole-3-carboxamide A solution of 0.50 g of the acid chloride obtained above in 10 ml of CH$_2$Cl$_2$ is added dropwise to a solution of 01.30 g of adamantan-2-amine hydrochloride and 0.41 ml of triethylamine in 10 ml of CH$_2$Cl$_2$, cooled to 0° C. The mixture is subsequently stirred at room temperature for 16 hours and then poured into 30 ml of iced water. The mixture is extracted with CH$_2$Cl$_2$ and the organic phase is washed successively with a 5% solution of HCl, water, a 5% solution of Na$_2$CO$_3$ and then a saturated solution of NaCl. After drying over MgSO$_4$ and evaporation of the solvent, the crude product is crystallized from hot benzene to give 0.32 g of white crystals.

M.p.=203° C.

EXAMPLE 2

N-(trans-4-Hydroxycyclohexyl)-1-(2,4-dichlorophenyl)-5-(4-chlorophenyl)-1H-pyrazole-3-carboxamide

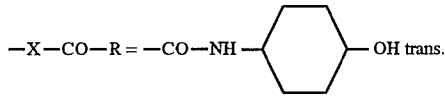

A) trans-4-Trimethylsilyloxycyclohexylamine

A solution of 1.85 ml of chlorotrimethylsilane in 10 ml of CH$_2$Cl$_2$ is added dropwise to a solution of 2.0 g of trans-4-hydroxycyclohexylamine hydrochloride and 4.05 ml of triethylamine in 20 ml of CH$_2$Cl$_2$, cooled to 0° C. After stirring for 16 hours at room temperature, the mixture is hydrolyzed with water and extracted. The organic phase is washed successively with water, a 5% solution of Na$_2$CO$_3$ and saturated NaCl. After drying over MgSO$_4$ and evaporation of the solvents, 1.43 g of amine (colorless liquid) are obtained.

B) N-(trans-4-Hydroxycyclohexyl)-1-(2,4-dichlorophenyl)-5-(4-chlorophenyl)-1H-pyrazole-3-carboxamide A solution of 0.60 g of the acid chloride prepared above according to Example 1D) in 10 ml of CH$_2$Cl$_2$ is added dropwise to a solution of 0.35 g of trans-4-trimethylsilyloxycyclohexylamine and 0.32 ml of triethylamine in 10 ml of CH$_2$Cl$_2$, cooled to 0° C. After stirring for 16 hours at room temperature, the mixture is poured into 30 ml of iced water and extracted with CH$_2$Cl$_2$. The organic phase is washed successively with 5% HCl and a saturated solution of NaCl and then dried over MgSO$_4$ and evaporated. The crude product is dissolved in 15 ml of THF; 15 ml of 5% HCl are added to the solution and the mixture is stirred for 1 hour. It is then extracted with ether and the extract is washed with water and then dried over MgSO$_4$, evaporated and crystallized from CH$_3$OH to give 0.20 g of the expected pyrazole.

M.p.=209° C.

The compounds described in TABLES I to XII below are prepared by the procedure of EXAMPLE 1 above, starting for example from the acid or ester derivatives described below in TABLE A.

TABLE A

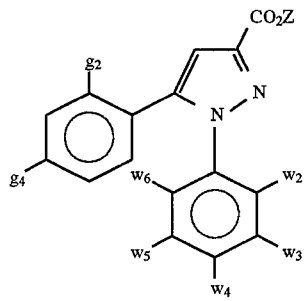

| $w_2$ | $w_3$ | $w_4$ | $w_5$ | $w_6$ | $g_2$ | $g_4$ | m.p.; °C. Z = H | m.p.; °C. Z = $CH_3$ |
|---|---|---|---|---|---|---|---|---|
| H | H | $CH_3$ | H | H | H | Cl | 185 | 98 |
| H | Cl | Cl | H | H | H | Cl | 162 | 147 |
| H | Cl | Cl | H | H | H | $CH_3$ | 188 | 145 |
| Cl | H | H | Cl | H | H | $CH_3$ | 232 | 132 |
| Cl | H | H | Cl | H | H | $CF_3$ | 214 | 179 |
| Cl | Cl | H | H | H | H | $CH_3$ | 214 | 101 |
| H | H | $CH_3$ | H | H | Cl | Cl | 188 | 102 |
| H | H | Cl | H | H | Cl | Cl | 224 | 118 |
| H | H | $OCH_3$ | H | H | H | Cl | 168 | — |
| Cl | H | Cl | H | Cl | H | Cl | 255 | 214 |
| Cl | H | Cl | H | H | H | 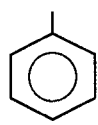 | 115 | 138 |

TABLE A-continued

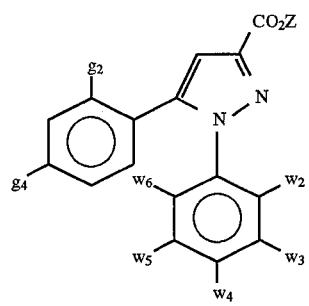

| $w_2$ | $w_3$ | $w_4$ | $w_5$ | $w_6$ | $g_2$ | $g_4$ | m.p.; °C. Z = H | m.p.; °C. Z = $CH_3$ |
|---|---|---|---|---|---|---|---|---|
| Cl | H | Cl | H | H | H | Br | 188 | 177 |
| H | H | $NO_2$ | H | H | H | $CH_3$ | 106 | 166 |

TABLE I

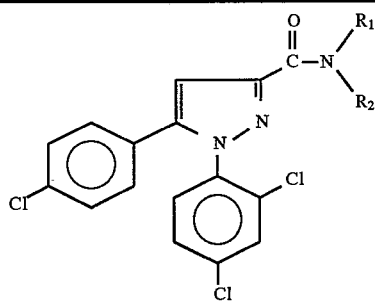 (Ia)

| Example n° | $-N\begin{smallmatrix}R_1\\R_2\end{smallmatrix}$ | m.p.; °C. or $[\alpha]_D^{20}$ Salt |
|---|---|---|
| 3 | $-NH-(CH_2)_2-CH_3$ | 100 |
| 4 | $-NH-(CH_2)_2-CH(C_6H_5)_2$ | 102 |
| 5 | $-NH-(CH_2)_3-C_6H_5$ | 60 |
| 6 | $-NH-(CH_2)_4-CH_3$ | 97 |

TABLE I-continued
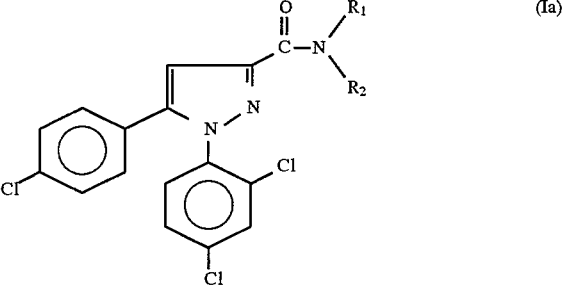
(Ia)
| Example n° | -N(R₁)(R₂) | m.p.; °C. or $[\alpha]_D^{20}$ Salt |
|---|---|---|
| 7 | -NH-CH(CH₃)₂ | 152 |
| 8 | -N(C₅H₁₁)₂ | (1) |
| 9 | -NH-cyclopropyl | 152 |
| 10 | -NH-cyclopentyl | 148 |
| 11 | -NH-cyclohexyl | 162 |
| 12 | -NH-cycloheptyl | 83 |
| 13 | -NH-cyclooctyl | 132 |
| 14 | -NH-(4-CH₃-cyclohexyl) trans | 186 |
| 15 | -NH-(4-CH₃-cyclohexyl) cis | 165 |
| 16 | -NH-(4-C₂H₅-cyclohexyl) | 134 |

TABLE I-continued (Ia) [Structure: 5-(4-chlorophenyl)-1-(2,4-dichlorophenyl)-pyrazole-3-carboxamide with N(R₁)(R₂)]

| Example n° | —N(R₁)(R₂) | m.p.; °C. or [α]$_D^{20}$ Salt |
|---|---|---|
| 17 | —NH—(4-methylcyclohexyl) | 144 |
| 18 | —NH—(2-methylcyclohexyl) | 174 |
| 19 | —NH—(2-methoxycyclohexyl) | 188 |
| 20 | —NH—(2,6-dimethylcyclohexyl) | 120 |
| 21 | —NH—(4-tert-butylcyclohexyl) trans | 208 |
| 22 | —NH—(4-tert-butylcyclohexyl) cis | 81 |
| 23 | —N(CH₃)(cyclohexyl) | 122 |
| 24 | —N(cyclohexyl)₂ | 188 |

TABLE I-continued
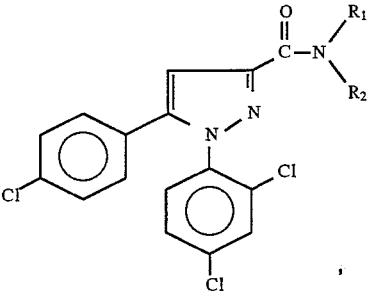
(Ia)
| Example n° | —N⟨R₁/R₂ | m.p.; °C. or $[\alpha]_D^{20}$ | Salt |
|---|---|---|---|
| 25 |  | 194 | |
| 26 | 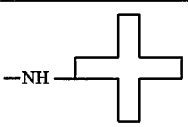 endo(+,−) | 190 | |
| 27 | endo(+) | 183 +14,1° | |
| 28 | endo(−) | 182 −14,1° | |
| 29 | 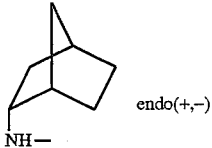 endo | 178 | |
| 30 | 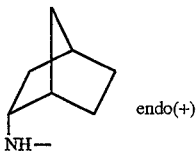 exo(+,−) | 191 | |
| 31 | 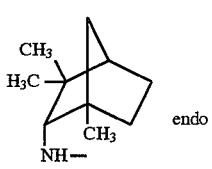 exo(+) | 185 +10,2° | |
| 32 | 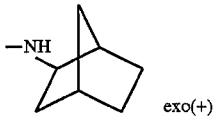 exo(−) | 184 −10,6° | |

TABLE I-continued
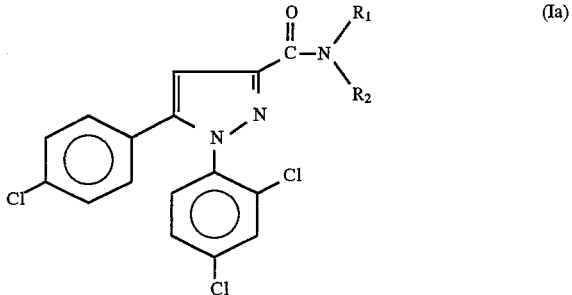
| Example n° | −N(R₁)(R₂) | m.p.; °C. or [α]_D^{20} Salt |
|---|---|---|
| 33 | 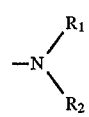 NH— exo | 170 |
| 34 | 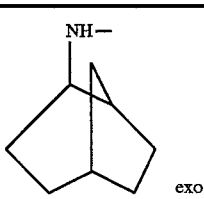 —NH exo | 198 |
| 35 | 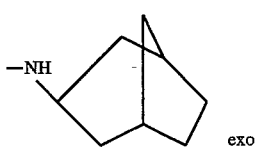 HN— endo | 182 |
| 36 | 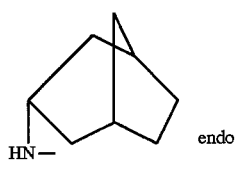 HN— Cl exo | 188 |
| 37 | 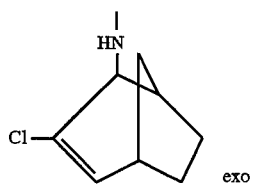 NH | 141 |
| 38 | 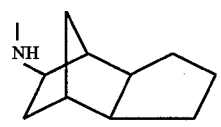 HN | 197 |
| 39 | 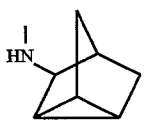 NH | 209 |

TABLE I-continued
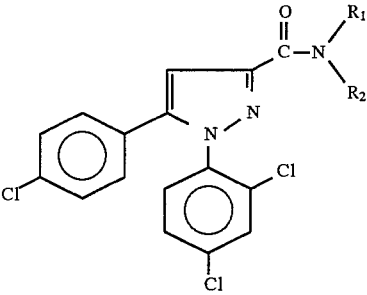
| Example n° | -N(R1)(R2) | m.p.; °C. or [α]$_D^{20}$ | Salt |
|---|---|---|---|
| 40 | 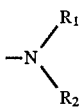 | 164 | |
| 41 | 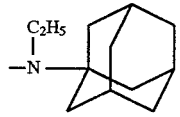 endo | 184 | |
| 42 | 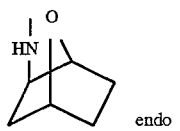 exo | 180 | |
| 43 | 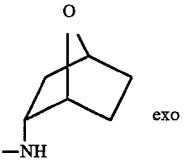 | 233 | |
| 44 | 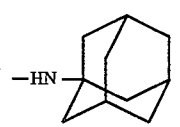 | 220 | |
| 45 | 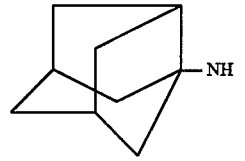 (+) | 156 +11,7° | |
| 46 | 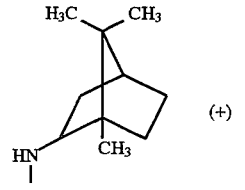 (−) | 151 −61,6° | |
| 47 | 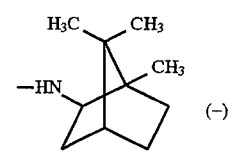 | 168 | |

TABLE I-continued
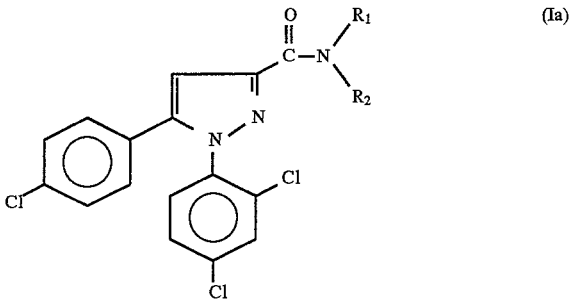
(Ia)
| Example n° | —N(R₁)(R₂) | m.p.; °C. or $[\alpha]_D^{20}$ Salt |
|---|---|---|
| 48 | —NH—(CH₂)₂—N(C₂H₅)(C₂H₅)(C₂H₅) | 108 |
| 49 | —NH—CH₂—cyclohexyl | 161 |
| 50 | —NH—(3-Cl-phenyl) | 154 |
| 51 | —NH—phenyl | 112 |
| 52 | —NH—(4-CH₃-phenyl) | 159 |
| 53 | —NH—CH₂—phenyl | 149 |
| 54 | —NH—(CH₂)₂—phenyl | 125 |
| 55 | —NH—CH₂—adamantyl | 220 |
| 57 | —NH—(CH₂)₂—(1-methylpyrrol-2-yl) | 158 |
| 58 | —NH—(CH₂)₂—(2-pyridyl) | 234 HCl |

TABLE I-continued
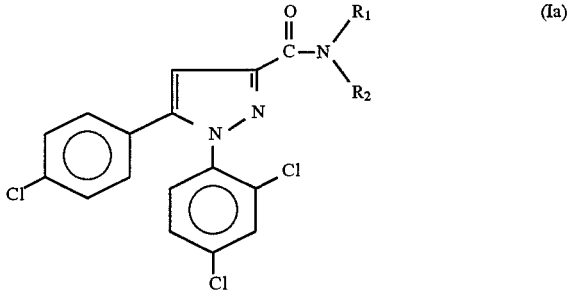
(Ia)
| Example n° | —N⟨R₁/R₂ | m.p.; °C. or [α]_D^{20} Salt |
|---|---|---|
| 59 | 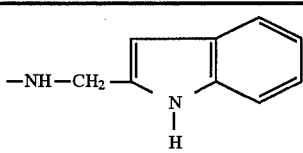 | 96 |
| 60 | 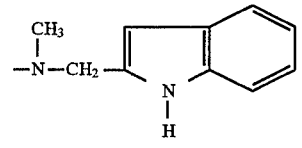 | 95 |
| 61 | 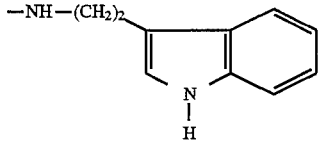 | 179 |
| 62 | 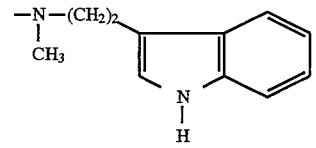 | 172 |
| 63 | 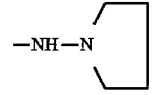 | 215 (dec) HCl |
| 64 | 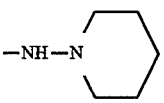 | 184 |
| 65 | 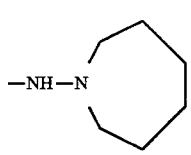 | 195 (dec) HCl |
| 66 | 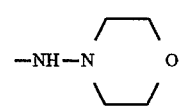 | 158 |
| 67 | 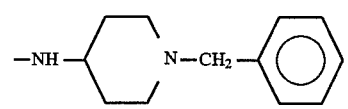 | 147 |

TABLE I-continued
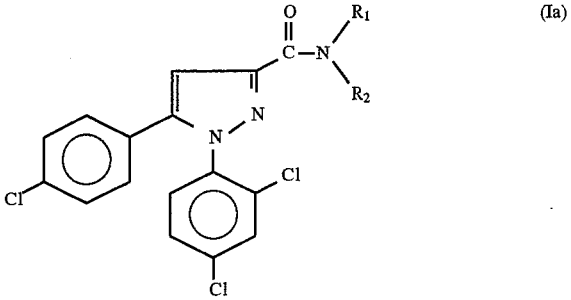
(Ia)
| Example n° | −N⟨R₁/R₂ | m.p.; °C. or $[\alpha]_D^{20}$ Salt |
|---|---|---|
| 68 | 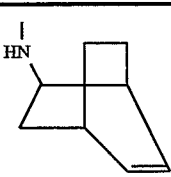 | 186 |
| 69 | 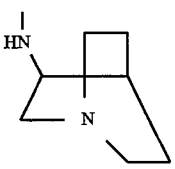 | 205 HCl |
| 70 |  | 136 |
| 71 | 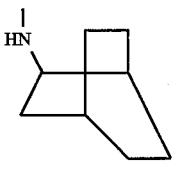 | 208 |
| 72 |  | 162 |
| 73 |  | 139 |
(1) NMR spectrum of the compound of Example 8 (200 MHz, DMSO $d^6$): 0.74 (3H, t, J = 5 Hz, CH₃); 0.91 (3H, t, J = 5 Hz, CH₃); 1.41–1.69 (12H, m, 6CH₂); 3.43 (2H, t, NCH₂); 3.66 (2H, s, NCH₂); 7.06 (1H, s, H pyrazole); 7.29 (2H, d, J = 8 Hz, H ar); 7.49 (2H, d, J = 8 Hz, H ar); 7.62–7.77 (2H, m, H ar); 7.92 (1H, d, J = 2 Hz, H ar).

TABLE II

Structure (Ia): 5-(4-chlorophenyl)-1-(4-methylphenyl)-1H-pyrazole-3-carboxamide with -N(R1)(R2)

| Example n° | -N(R1)(R2) | m.p.; °C. |
|---|---|---|
| 74 | —NH—(CH$_2$)$_2$—CH$_3$ | 95 |
| 75 | —NH—CH(CH$_3$)$_2$ | 114 |
| 76 | —N(C$_5$H$_{11}$)(C$_5$H$_{11}$) | 59 |
| 77 | —NH—CH$_2$-(1H-indol-2-yl) | 175 |
| 78 | —NH—(CH$_2$)$_2$-(1H-indol-3-yl) | 178 |
| 79 | —N(CH$_3$)—(CH$_2$)$_2$-(1H-indol-3-yl) | 175 |
| 80 | pyrrolidin-1-yl | 147 |

TABLE III

Structure (Ia): 5-(4-methylphenyl)-1-(3,4-dichlorophenyl)-1H-pyrazole-3-carboxamide with -N(R1)(R2)

| Example n° | -N(R1)(R2) | m.p.; °C. |
|---|---|---|
| 81 | —NH-cyclohexyl | 144 |
| 82 | —NH-(2-methylcyclohexyl) trans | 165 |
| 83 | —NH-(2-methylcyclohexyl) cis | 143 |
| 84 | —NH-(2-methylcyclohexyl) | 155 |
| 85 | —NH-(3-methylcyclohexyl) | 153 |
| 86 | —NH-(2,3-dimethylcyclohexyl) | 129 |
| 87 | —NH-(2-methoxycyclohexyl) | 140 |
| 88 | —NH-(2,6-dimethylcyclohexyl) | 148 |

TABLE III-continued (Ia) Structure: 5-(4-methylphenyl)-1-(3,4-dichlorophenyl)-pyrazole-3-carboxamide with -N(R₁)(R₂)

| Example n° | -N(R₁)(R₂) | m.p.; °C. |
|---|---|---|
| 89 | -N(CH₃)-cyclohexyl | 137 |
| 90 | -N(C₂H₅)-cyclohexyl (cis + trans) | 63 |
| 91 | -NH-norbornyl exo(+,-) | 156 |
| 92 | -NH-norbornyl exo(-) | 149 -15,1° |
| 93 | -NH-norbornyl exo(+) | 149 +15,1° |
| 94 | -N(CH₃)-norbornyl exo | (2) |
| 95 | -N(C₂H₅)-norbornyl exo | 48 |
| 96 | -N(CH₂CH₂CH₃)-norbornyl exo | 57 |
| 97 | -NH-(1,7,7-trimethylnorbornyl) endo | 157 |
| 98 | -NH-norbornyl exo | 168 |
| 99 | -NH-(chloro-norbornenyl) exo | 156 |
| 100 | -NH-(CH₂)₂-phenyl | 112 |

(2) NMR spectrum of the compound of Example 94 (200 MHz, DMSO d⁶):
1.14–1.80 (10H, m, norbornyl); 2.34 (3H, s, CH₃ tolyl); 3.12 (3H, sb, NCH₃);
4.40 (1H, t, N—CH norbornyl); 6.90 (1H, s, H pyrazole); 7.23–7.31 (2H, m, H ar); 7.71–7.77 (5H, m, H ar).

TABLE IV (Ia) Structure: 5-(4-chlorophenyl)-1-(3,4-dichlorophenyl)-pyrazole-3-carboxamide with -N(R₁)(R₂)

| Example n° | -N(R₁)(R₂) | m.p.; °C. |
|---|---|---|
| 101 | -NH-cyclohexyl | 154 |

TABLE IV-continued

Structure (Ia): 5-(4-chlorophenyl)-1-(3,4-dichlorophenyl)-1H-pyrazole-3-carboxamide with -N(R₁)(R₂) group.

| Example n° | -N(R₁)(R₂) | m.p.; °C. |
|---|---|---|
| 102 | -NH-cyclohexyl-2-CH₃ | 149 |
| 103 | -N(CH₃)-cyclohexyl | 136 |
| 104 | -NH-norbornyl (exo) | 165 |
| 105 | -N(C₂H₅)-norbornyl (exo) | 134 |

TABLE V

Structure (Ia): 5-(4-methylphenyl)-1-(2,5-dichlorophenyl)-1H-pyrazole-3-carboxamide with -N(R₁)(R₂) group.

| Example n° | -N(R₁)(R₂) | m.p.; °C. |
|---|---|---|
| 106 | -NH-cyclohexyl | 205 |
| 107 | -NH-cyclohexyl-2-CH₃ | 175 |
| 108 | -N(CH₃)-cyclohexyl | 214 |
| 109 | -NH-norbornyl (exo) | 240 |
| 110 | -N(C₂H₅)-norbornyl (exo) | 124 |
| 111 | -N(CH₂CH₂CH₃)-norbornyl (exo) | 124 |

TABLE VI
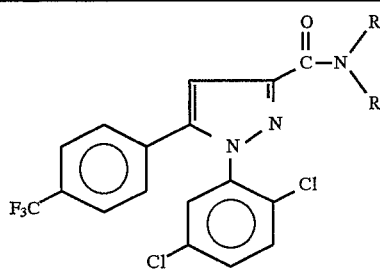
| Example n° | −N(R1)(R2) | m.p.; °C. |
|---|---|---|
| 112 | 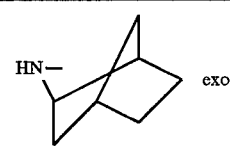 exo | 215 |
| 113 | 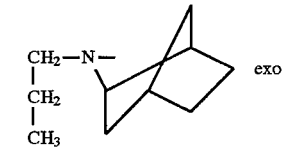 exo | 55 |
| 114 | 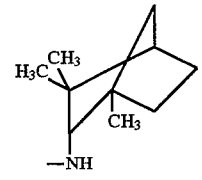 | 168 |
TABLE VII
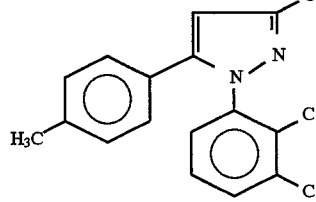
| Example n° | −N(R1)(R2) | m.p.; °C. |
|---|---|---|
| 115 | 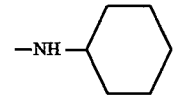 | 193 |
| 116 | 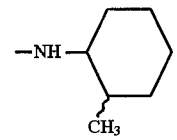 | 168 |
TABLE VII-continued
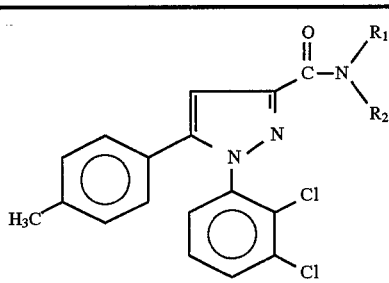
| Example n° | −N(R1)(R2) | m.p.; °C. |
|---|---|---|
| 117 | 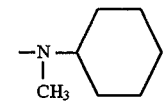 | 152 |
| 118 | 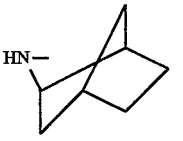 exo | 216 |
| 119 | 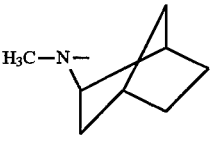 exo | 154 |
| 120 | 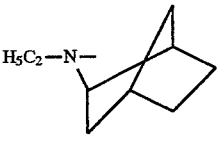 exo | 102 |
TABLE VIII
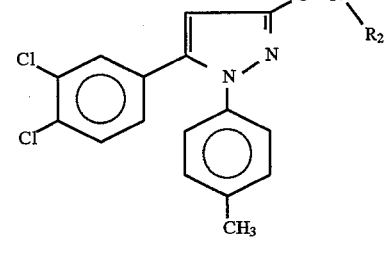
| Example n° | −N(R1)(R2) | m.p.; °C. |
|---|---|---|
| 121 | 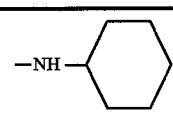 | 146 |

TABLE VIII-continued

Structure (Ia): 5-(3,4-dichlorophenyl)-1-(4-methylphenyl)-1H-pyrazole-3-carboxamide with -N(R₁)(R₂) at C=O.

| Example n° | -N(R₁)(R₂) | m.p.; °C. |
|---|---|---|
| 122 | -NH-(2-methylcyclohexyl) | 115 |
| 123 | -N(CH₃)-cyclohexyl | 119 |
| 124 | HN-(norbornyl) exo | 115 |
| 125 | H₅C₂-N-(norbornyl) exo | 112 |

TABLE IX

Structure (Ia): 5-(3,4-dichlorophenyl)-1-(4-chlorophenyl)-1H-pyrazole-3-carboxamide with -N(R₁)(R₂).

| Example n° | -N(R₁)(R₂) | m.p.; °C. |
|---|---|---|
| 126 | HN-cyclohexyl | 150 |

TABLE IX-continued

| Example n° | -N(R₁)(R₂) | m.p.; °C. |
|---|---|---|
| 127 | HN-(2-methylcyclohexyl) | 142 |
| 128 | HN-(norbornyl) exo | 159 |
| 129 | H₅C₂-N-(norbornyl) exo | 108 |

TABLE X

Structure (Ia): 5-(4-chlorophenyl)-1-(4-methoxyphenyl)-1H-pyrazole-3-carboxamide with -N(R₁)(R₂).

| Example n° | -N(R₁)(R₂) | m.p.; °C. |
|---|---|---|
| 130 | -NH-(CH₂)₂-CH₃ | 144 |
| 131 | -NH-CH(CH₃)₂ | 115 |
| 132 | -NH-cyclohexyl | 123 |

TABLE X-continued
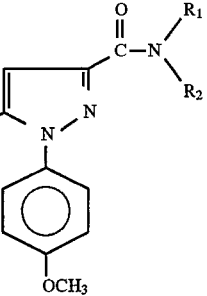
(Ia)
| Example n° | —N(R1)(R2) | m.p.; °C. |
|---|---|---|
| 133 | 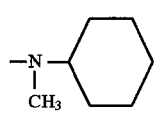 | 108 |
| 134 | 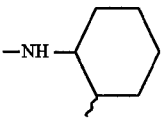 | 120 |
| 135 | 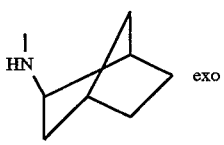 exo | 169 |
| 136 | 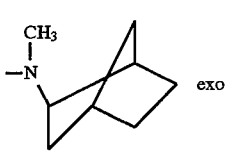 exo | 68 |
| 137 |  exo | 58 |
| 138 | 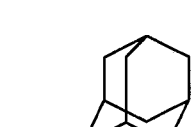 | 182 |
| 139 | 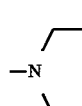 | 152 |
TABLE XI
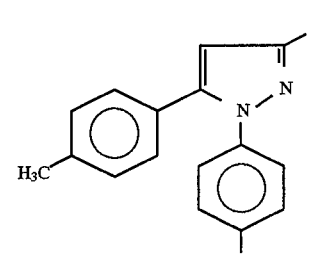
| Example n° | —N(R1)(R2) | m.p.; °C. |
|---|---|---|
| 140 | 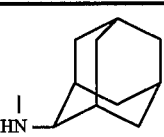 | 260 |
| 141 | 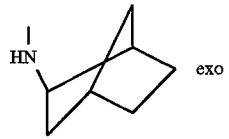 exo | 191 |
| 142 | 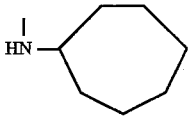 | 182 |
TABLE XII
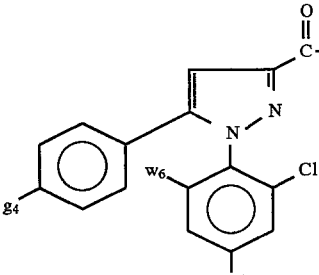
(Ia)
| Example n° | —N(R1)(R2) | g4 | w6 | m.p.; °C. |
|---|---|---|---|---|
| 143 | 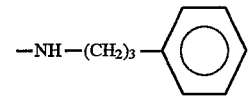 —NH—(CH2)3—Ph | Br | H | 130 |
| 144 | 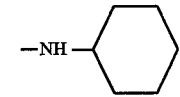 —NH-cyclohexyl | Cl | Cl | 224 |

TABLE XII-continued (Ia)

[Structure: pyrazole carboxamide with phenyl (g4 substituent), N-phenyl with Cl at position and w6 substituent, C(=O)-NR1R2]

| Example n° | -N(R1)(R2) | g4 | w6 | m.p.; °C. |
|---|---|---|---|---|
| 145 | -NH-cycloheptyl | Br | H | 148 |
| 146 | -NH-(2-adamantyl) | Cl | Cl | 245 |
| 147 | -NH-(2-adamantyl) | Br | H | 206 |
| 148 | HN-norbornyl exo | Cl | Cl | 231 |
| 149 | HN-norbornyl exo | Br | H | 201 |
| 150 | norbornyl exo, NH-phenyl | | H | 165 |
| 151 | HN-bicyclooctyl | | Br | H | 209 |
| 152 | -NH-(2-adamantyl), phenyl | | H | 204 |

EXAMPLE 153

N-(2-Adamantyl)-1-(2,4-dichlorophenyl)-4-methyl-5-(4-chlorophenyl)-1H-pyrazole-3-carboxamide

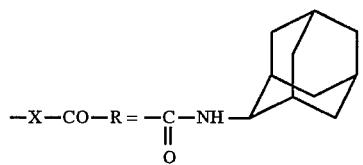

$-X-CO-R = -\overset{\underset{\parallel}{O}}{C}-NH-$ (adamantyl)

A) Lithium salt of ethyl 2,4-dioxo-(4-chlorophenyl)butanoate 60 ml of a 1.0M solution of the lithium salt of hexamethyldisilazane in THF are introduced into 240 ml of anhydrous ether. The mixture is cooled to –78° C. and a solution of 10.12 g of 4-chloropropiophenone in 50 ml of ether is introduced dropwise. After stirring for 30 minutes at –78° C., a solution of 9.16 ml of diethyl oxalate in 50 ml of ether is introduced rapidly, the temperature is then allowed to rise and the mixture is stirred for 5 hours at room temperature. The pale yellow precipitate formed is filtered off, washed with ether and dried under vacuum to give 6.32 g of the expected salt.

B) Ethyl 1-(2,4-dichlorophenyl)-4-methyl-5-(4-chlorophenyl)-1H-pyrazole-3-carboxylate This ester is obtained in the same way as in Example 1B) from the lithium salt obtained above, and is purified by recrystallization from isopropyl ether.

M.p.=105° C.

C) Compound 153

This amide is obtained from the above ester in the same way as in Example 1C), 1D) and 1E) by conversion of the ester to the acid chloride, reaction of the latter with adamantan-2-amine and purification by recrystallization from isopropyl ether.

M.p.=190° C.

The amides described in TABLE XIII below are prepared by the procedure of Example 153 above.

TABLE XIII (Ia)

[Structure: 4-methyl pyrazole-3-carboxamide with 4-chlorophenyl at 5-position and 2,4-dichlorophenyl on N1]

| Example n° | NH-R2 | m.p.; °C. |
|---|---|---|
| 154 | -NH-cyclohexyl | 78 |
| 155 | -NH-norbornyl exo | 85 |

TABLE XIII-continued (Ia)

[Structure: pyrazole core with H3C, C(=O)-NH-R2, 4-chlorophenyl and 2,4-dichlorophenyl substituents]

| Example n° | NH—R₂ | m.p.; °C. |
|---|---|---|
| 156 | [norbornyl-NH] | 148 |
| 157 | [N-methyl norbornyl HN-] | 155 |
| 158 | [adamantyl HN-] | 201 |

EXAMPLE 159

N-[1-(para-Tolyl)-5-(4-chlorophenyl)-1H-pyrazol-3-ylmethyl]-N-methylcyclohexylcarboxamide

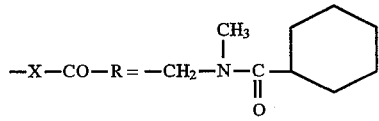

A) N-Methyl-1-(p-tolyl)-5-(4-chlorophenyl)-1H-pyrazole-3-carboxamide

A solution of 0.50 g of 1-(4-methylphenyl)-5-(4-chlorophenyl)pyrazole-3-carboxylic acid chloride in ml of $CH_2Cl_2$ is added dropwise to 100 ml of a 33% solution of methylamine in ethanol. After stirring for hours at room temperature, the mixture is concentrated under vacuum, the residue is taken up with a mixture of 5% $Na_2CO_3$+AcOEt, the organic phase is decanted, washed with a saturated solution of NaCl and dried over $MgSO_4$ and the solvents are evaporated off. The residue is taken up in isopropyl ether and the crystals obtained are filtered off and dried under vacuum to give 0.44 g of the expected amide.

M.p.=138° C.

B) N-Methyl-[1-(p-tolyl)-5-(4-chlorophenyl)-1H-pyrazol-3-yl]methylamine

A solution of 8.76 g of the amide obtained above in 25 ml of anhydrous THF is added dropwise, at a temperature between 0° and 5° C., to 75 ml of a 1.0M solution of $BH_3$ in THF. After the reaction mixture has returned to room temperature, it is refluxed for 16 hours and 18 ml of 6 N HCl are then run in, while cooling with an ice bath. The mixture is stirred for 1 and a half hours at room temperature, the THF is then distilled and the residue is concentrated under vacuum. The reaction mixture is then rendered alkaline to pH 9–10 with NaOH pellets; extraction is carried out with ethyl acetate, the extract is dried over $MgSO_4$, the solvents are evaporated off and the crude product obtained is purified by chromatography on silica gel (300 g) using $CH_2Cl_2$/$CH_3OH$ 97/3 (v/v) as the eluent to give 6.0 g of amine.

M.p.=85° C.

C) Compound 159

0.62 ml of triethylamine and then a solution of 0.23 g of cyclohexanoic acid chloride in 5 ml of $CH_2Cl_2$ are added successively to a solution of 0.46 g of the above amine in 10 ml of $CH_2Cl_2$. After stirring for 15 minutes at room temperature, the reaction mixture is concentrated under vacuum and the residue is taken up in 30 ml of water and extracted with ethyl acetate. The organic phase is washed successively with 5% $Na_2CO_3$, water and then a saturated solution of NaCl and dried over $MgSO_4$ and the solvents are then evaporated off. The crude product is purified by chromatography on silica gel (25 g) using toluene/AcOEt 70/30 (v/v) as the eluent. The pure product fractions are concentrated under vacuum and the residue is recrystallized from isopropyl ether to give 0.38 g of amide.

M.p.=124° C.

The amides described in TABLES XIV and XV below are prepared by the procedure of EXAMPLE 159 above.

TABLE XIV (Ib)

[Structure: pyrazole with CH₂-N(R₃)-C(=O)-R₂, 4-chlorophenyl and 2,4-dichlorophenyl substituents]

| Example n° | —N(R₃)—C(=O)—R₂ | m.p.; °C. |
|---|---|---|
| 160 | —NH—C(=O)-cyclohexyl | 178 |
| 161 | —NH—C(=O)-cycloheptyl | 148 |
| 162 | —NH—C(=O)-adamantyl | 148 |
| 163 | —N(CH₃)—C(=O)-cyclohexyl | 123 |

TABLE XIV-continued

Structure (Ib): pyrazole with CH₂—N(R₃)—C(=O)—R₂ at 3-position, 4-chlorophenyl at 5-position, and 2,4-dichlorophenyl on N1.

| Example n° | —N(R₃)—C(=O)—R₂ | m.p.; °C. |
|---|---|---|
| 164 | —NH—C(=O)—(4-chlorophenyl) | 142 |
| 165 | —NH—C(=O)—(anthracen-9-yl) | 175 |
| 166 | —NH—C(=O)—(1H-indol-2-yl) | 225 |
| 167 | —N(CH₃)—C(=O)—(1H-indol-2-yl) | 155 |
| 168 | —NH—C(=O)—(5-methoxy-1H-indol-2-yl) | 228 |

TABLE XV

Structure (Ib): pyrazole with CH₂—N(R₃)—C(=O)—R₂ at 3-position, 4-chlorophenyl at 5-position, and 4-methylphenyl on N1.

| Example n° | —N(R₃)—C(=O)—R₂ | m.p.; °C. |
|---|---|---|
| 169 | —NH—C(=O)—cyclohexyl | 103 |
| 170 | —NH—C(=O)—(1H-indol-2-yl) | 166 |
| 171 | —N(CH₃)—C(=O)—(1H-indol-2-yl) | 165 |

EXAMPLE 172

N-[1-(2,4-Dichlorophenyl)-5-(4-chlorophenyl)-1H-pyrazol-3-ylmethyl]-N'-(4-chlorophenyl)urea —X—CO—R = —CH₂—NH—C(=O)—NH—(4-chlorophenyl)

A) 1-(2,4-Dichlorophenyl)-5-(4-chlorophenyl)-1H-pyrazole-3-carboxamide

This amide is obtained in the same way as in Example 159A) by reacting the acid chloride described in Example 1D) with a saturated solution of ammonia in ethanol.
M.p.=178° C.

B) [1-(2,4-Dichlorophenyl)-5-(4-chlorophenyl)-1H-pyrazol-3-yl]methylamine

This amine is obtained in the same way as in Example 159B) by reducing the amide obtained above with $BH_3$ in THF.

C) Compound 172

0.20 g of 4-chlorophenyl isocyanate is added to a solution of 0.45 g of the above amine in 10 ml of toluene and the reaction mixture is stirred at room temperature for 16 hours. The solvent is evaporated off, the residue is taken up in 20 ml of ethyl acetate, washed with water and then dried over MgSO$_4$ and the solvents are evaporated off. The residue is purified by chromatography on silica gel (20 g) using toluene/AcOEt 60/40 (v/v) as the eluent. Concentration of the pure product fractions gives a residue, which is recrystallized from an isopropanol/isopropyl ether mixture to give 0.18 g of the expected urea.

M.p.=172° C.

The ureas described in TABLE XVI below are prepared by the procedure of EXAMPLE 172 above.

TABLE XVI

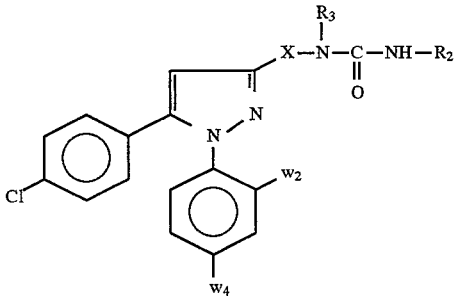

(Ic)

| Example n° | $-X-N(R_3)-C(=O)-NH-R_2$ | w$_2$ | w$_4$ | m.p.; °C. |
|---|---|---|---|---|
| 173 | —CH$_2$—NH—C(=O)—NH—cyclohexyl | Cl | Cl | 122 |
| 174 | —CH$_2$—NH—C(=O)—NH—C$_6$H$_5$ | Cl | Cl | 88 |
| 175 | —CH$_2$—NH—C(=O)—NH—C$_6$H$_4$—CH$_3$ | Cl | Cl | 120 |
| 176 | —CH$_2$—N(CH$_3$)—C(=O)—NH—C$_6$H$_4$—Cl | Cl | Cl | 157 |
| 177 | —CH$_2$—NH—C(=O)—NH—C$_6$H$_3$(Cl)$_2$ | Cl | Cl | 157 |
| 178 | —CH$_2$—NH—C(=O)—NH—C$_6$H$_4$—OCH$_3$ | Cl | Cl | 138 |
| 179 | —CH$_2$—NH—C(=O)—NH—C$_6$H$_4$—Cl | H | CH$_3$ | 183 |
| 180 | —CH$_2$—N(CH$_3$)—C(=O)—NH—C$_6$H$_4$—Cl | H | CH$_3$ | 148 |

EXAMPLE 181

N-[1-(2,4-Dichlorophenyl)-5-(4-chlorophenyl)-1H-pyrazol-3-yl]cyclohexylcarboxamide

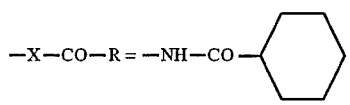

A) N-(tert-Butoxycarbonyl)-[1-(2,4-dichlorophenyl)-5-(4-chlorophenyl)-1H-pyrazol-3-yl]amine 3.25 g of the 1-(2,4-dichlorophenyl)-5-(4-chlorophenyl) pyrazole-3-carboxylic acid obtained according to Example 1C) and then 1.32 ml of triethylamine are added to a solution of 2.05 ml of diphenylphosphoryl azide in 40 ml of anhydrous t-butanol and the reaction mixture is refluxed under nitrogen for 12 hours. After cooling, it is treated with a saturated solution of $NaHCO_3$ and extracted with ethyl acetate. After washing with water and then with a saturated solution of NaCl, drying over $MgSO_4$ and evaporation of the solvents, the crude product is purified by chromatography on 70–230 mesh silica gel using $CH_3OH/CH_2Cl_2$ 1/99 (v/v) as the eluent to give 1.09 g of the expected product.

B) 1-(2,4-Dichlorophenyl)-5-(4-chlorophenyl)-1H-pyrazol-3-ylammonium hydrochloride 1.09 g of the above product are dissolved in 20 ml of a saturated solution of HCl in EtOH, diluted to 50%, and the reaction mixture is refluxed for 2 hours. The solvent is then evaporated off and the residue is triturated in ethyl acetate under reflux and then filtered off and dried under vacuum to give 0.55 g of the hydrochloride.

C) Compound 181

A solution of 0.11 ml of cyclohexanecarboxylic acid chloride in 2 ml of $CH_2Cl_2$ is added dropwise to a solution of 0.20 g of the hydrochloride obtained in the previous Example and 0.19 ml of triethylamine in 5 ml of $CH_2Cl_2$. After stirring for 24 hours at room temperature, the mixture is washed successively with a 5% solution of HCl, water, a 5% solution of $Na_2CO_3$ and then a saturated solution of NaCl and dried over $MgSO_4$ and the solvents are then evaporated off. The crude product is crystallized from $iPr_2O$ to give 0.12 g of the expected amide.

M.p.=213° C.

EXAMPLE 182

N-Methyl-N-[1-(2,4-dichlorophenyl)-5-(4-chlorophenyl)-1H-pyrazol-3-yl]adamantyl-1-carboxamide

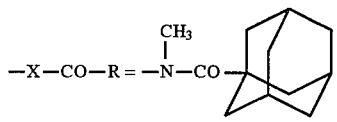

A) N-[1-(2,4-Dichlorophenyl)-5-(4-chlorophenyl)-1H-pyrazol-3-yl]formamide 0.50 g of 1-(2,4-dichlorophenyl)-5-(4-chlorophenyl)-1H-pyrazol-3-ylamine, obtained in the previous Example, is added in small portions to a mixture of 4 ml of formic acid and 0.5 ml of acetic anhydride, cooled in an ice bath. After stirring for 30 min, the solvents are evaporated off under vacuum and the residue is taken up in isopropyl ether. The white solid obtained is filtered off, washed with isopropyl ether and dried under vacuum to give 0.49 g of the expected formamide.

M.p.=181° C.

B) N-Methyl-[1-(2,4-dichlorophenyl)-5-(4-chlorophenyl)-1H-pyrazol-3-yl]amine A solution of 1.15 g of the formamide obtained in the previous Example in 10 ml of anhydrous THF is added dropwise, at room temperature, to a suspension of 0.24 g of $LiAlH_4$ in 40 ml of anhydrous THF. The mixture is then refluxed for 20 minutes, cooled to 0° C. and hydrolyzed with 0.24 ml of water, then 0.24 ml of 15% NaOH and then 0.72 ml of water. After stirring for 20 minutes at room temperature, the mixture is filtered, the material on the filter is washed with THF and the filtrate is evaporated to dryness. The residue is taken up in isopropyl ether, filtered off and dried under vacuum to give 1.02 g of the expected amine.

M.p.=157° C.

C) Compound 182

By following the procedure of Example 181C), reaction of the amine obtained above with adamantane-1-carboxylic acid chloride gives the expected amide, which is purified by chromatography on a silica column using AcOEt/toluene 7:93 as the eluent.

M.p.=65° C.

TABLE XVII

| Example n° | R₃ | R₂ | m.p.; °C. |
|---|---|---|---|
| 183 | H | (adamantyl) | 284 |
| 184 | H | (2-methylindol-3-yl) | 291 |
| 185 | H | —CH₂—(4-chlorophenyl) | 164 |
| 186 | CH₃ | (cyclohexyl) | 127 |

EXAMPLE 187

N-Methyl-[1-(2,4-dichlorophenyl)-5-(4-chlorophenyl)-1H-pyrazol-3-yl]-N'-(4-chlorophenyl)urea —X—CO—R = —NH—CO—NH—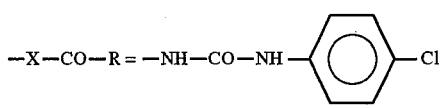—Cl 225 mg of 4-chlorophenyl isocyanate are added to a suspension of 0.40 g of 1-(2,4-dichlorophenyl)-5-(4-chlorophenyl)-1H-pyrazol-3-ylamine, obtained by neutralizing the hydrochloride obtained in Example 181B), in 15 ml of toluene and the mixture is heated at 40° C. for 1 hour and then left to react at room temperature for 16 hours. The precipitate obtained is filtered off, washed with toluene and dried under vacuum to give 0.46 g of the expected urea. M.p.=215° C.

EXAMPLE 188

N-[1-(2,4-Dichlorophenyl)-5-(4-chlorophenyl)-1H-pyrazol-3-yl]-N'-(1-adamantyl)urea —X—CO—R = NH—CO—NH—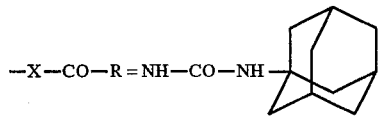

A) A solution of 2.54 g of sodium azide in 10 ml of water is added to a solution of 10.0 g of the acid chloride obtained according to Example 1D) in 320 ml of acetone, cooled to 0° C. After stirring for 1 hour at 0° C., the precipitate obtained is filtered off, washed with acetone and then dried under vacuum to give 9.86 g of the expected acyl azide.

B) N-[1-(2,4-Dichlorophenyl)-5-(4-chlorophenyl)-1H-pyrazol-3-yl]-N'-(1-adamantyl)urea A solution of 1.00 g of the acyl azide obtained in the previous Example in 5 ml of toluene is refluxed for 30 minutes. After it has returned to room temperature, the resulting solution of isocyanate is treated with 0.39 g of adamantan-1-amine and the mixture is stirred for 1 and a half hours. The precipitate obtained is filtered off, washed with toluene and then isopropyl ether and subsequently purified by trituration in an acetone/methanol mixture. After drying under vacuum, 0.48 g of the expected urea is obtained.

M.p.=244° C.

TABLE XVIII

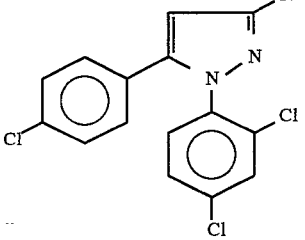

(Ie)

| Example n° | $R_3$ | $R_2$ | m.p.; °C. |
|---|---|---|---|
| 189 | H | 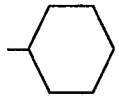 | 227 |
| 190 | $CH_3$ | 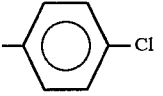—Cl | 144 |

EXAMPLE 191

1-Cyclohexylmethyl [1-(2,4-dichlorophenyl)-5-(4-chlorophenyl)-1H-pyrazol-3-yl]ketone —X—CO—R = —CO—CH₂—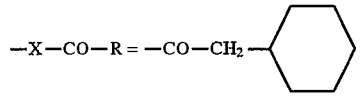

2.5 ml of a 0.625M solution of $MnLi_2Cl_4$ in THF (Tetrahedron, 1989, 45, 4163) are cooled to 0° C., 3.12 ml of a 0.50M solution of methylcyclohexylmagnesium bromide in THF are added dropwise and the reaction mixture is then stirred at 0° C. for 2 hours. It is then cooled to −10° C. and a solution of 0.50 g of the acid chloride prepared according to Example 1D) in 8 ml of THF is added dropwise. The mixture is stirred at room temperature for 5 hours and then hydrolyzed with a saturated solution of $NH_4Cl$ and extracted with ether and the extract is washed with water and then with a saturated solution of NaCl. After drying over $MgSO_4$ and evaporation of the solvents, the crude product is purified by chromatography on 230–400 mesh silica gel using AcOEt/hexane 5/95 (v/v) as the eluent to give 0.09 g of the expected ketone.

M.p.=118° C.

EXAMPLE 192

1-[1-(2,4-Dichlorophenyl)-5-(4-chlorophenyl)-1H-pyrazol-3-yl]-2-(4-methylphenyl)ethan-1-one —X—CO—R = —COCH₂—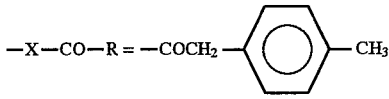—CH₃

A) 1-(2,4-Dichlorophenyl)-3-cyano-5-(4-chlorophenyl)-pyrazole

A solution of 0.70 g of 1-(2,4-dichlorophenyl)-5-(4-chlorophenyl)-1H-pyrazole-3-carboxamide, obtained according to Example 172A), and 0.74 ml of mesyl chloride in 6 ml of pyridine is heated at 50° C. for 8 hours. The solvent is evaporated off under vacuum and the residue is dissolved in 20 ml of $CH_2Cl_2$. The resulting solution is washed successively with a 5% solution of HCl, then water and then a saturated solution of NaCl and dried over $MgSO_4$ and the solvent is then evaporated off. The residue is crystallized from isopropyl ether to give 0.66 g of the expected nitrile.

M.p.=123° C.

B) Compound 292

6.3 ml of a 1.0M solution of 4-methylbenzylmagnesium chloride in ethyl ether are added dropwise to a solution of 0.73 g of the above nitrile in 20 ml of ethyl ether. After a reaction time of 2 hours at room temperature, the mixture is hydrolyzed with 50 ml of 5% hydrochloric acid and the resulting two-phase mixture is stirred for 30 minutes. The pink precipitate formed is filtered off, washed with water and ethyl ether and then dissolved in 100 ml of $CH_2Cl_2$ and the solution is stirred for 30 minutes in the presence of about 10 g of moist silica. The silica is then filtered off, the liltrate is evaporated and the residue is crystallized from a $CH_2Cl_2$/$iPr_2O$ mixture to give 0.37 g of the expected ketone.

M.p.=175° C.

TABLE XIX

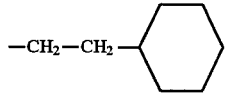

| Example n° | $R_5$ | m.p.; °C. |
|---|---|---|
| 193 | —CH$_2$—CH$_2$—(cyclohexyl) | 129 |
| 194 | —CH$_2$—(norbornyl) | 152 |

EXAMPLE 195

N-piperidino-5-(4-chlorophenyl)-1-(2,4-dichlorophenyl)-4-methyl-pyrazole-3-carboxamide A) Lithium salt of ethyl 4-(4-chlorophenyl)-3-methyl-4-oxydo-2-oxobuten-3-oate 125 ml of a 1M solution of the lithium salt of hexamethyldisilazane in THF are added under a nitrogen atmosphere to 500 ml of ether. The mixture is cooled to −78° C. and a solution of 21 g of 4-chloropropiophenone in 100 ml of ether is added dropwise. After stirring for 45 minutes, 19.2 ml of ethyl oxalate are added rapidly and the mixture is stirred for 16 hours while allowing the temperature to rise to room temperature. The precipitate formed is filtered off, washed with ether and dried under vacuum to give 12.6 g of the expected product.

B) Ethyl 5-(4-chlorophenyl)-1-(2,4-dichlorophenyl)-4-methyl-pyrazole-3-carboxylate 9.8 g of 2,4-dichlorophenylhydrazine are added to a solution of 12.6 g of the lithium salt obtained above in 70 ml of ethanol and the mixture is stirred for 16 hours at room temperature. The precipate formed is filtered off, washed with ethanol and then ether and dried under vacuum to give 12.6 g of hydrazone. This is dissolved in 100 ml of acetic acid, the mixture is refluxed for 24 hours and then poured into 500 ml of iced water. The mixture is extracted with ethyl acetate, washed with water and then a saturated solution of NaCl. After drying over magnesium sulfate and evaporation under vacuum, the crude product is crystallized from isopropyl ether to give 9.6 g of the expected product. m.p.=124° C.

C) 5-(4-chlorophenyl)-1-(2,4-dichlorophenyl)-4-methyl-pyrazole-3-carboxylic acid A solution of 3.3 g of KOH in 70 ml of water is added to a solution of 9.6 g of the ester obtained above in 70 ml of methanol. The mixture is refluxed for 3 hours, poured into 200 ml of iced water and the reaction mixture is acidified to pH=1 upon addition of a 10% solution of HCl. The precipitate formed is filtered off, washed with water and dried under vacuum to give 0 8.8 g of the expected acid. m.p.=211° C.

D) 5-(4-chlorophenyl)-1-(2,4-dichlorophenyl)-4-methyl-pyrazole-3-carboxylic acid chloride 5 ml of thionyl chloride are added to a suspension of 8.8 g of the acid obtained above in 90 ml of toluene, the mixture is refluxed for 3 hours and then evaporated to dryness under vaccum. The residue is taken up in 90 ml of toluene and the solvent is evaporated off again to give 8.0 g of the expected acid chloride which is used as such in the following step.

E) N-piperidino-5-(4-chlorophenyl)-1(2,4-dichlorophenyl)-4-methyl-pyrazole-3-carboxamide A solution of 8.0 g of the acid chloride obtained above in 80 ml of dichloromethane is added dropwise to a solution of 2.8 ml of 1-aminopiperidine and 3.6 ml of triethylamine in 100 ml of dichloromethane, cooled to 0° C. The reaction mixture is stirred for 3 hours while allowing the temperature to rise to room temperature and then poured into 200 ml of iced water. The mixture is extracted with dichloromethane, washed with water and then a saturated solution of NaCl, dried over $MgSO_4$ and evaporated under vaccum. The residue is purified by chromatography on silica gel using AcOEt/toluene (10/90; v/v) as the eluent. Crystallisation in isopropyl ether gives 5.9 g of the expected product.

m. p.=148° C.

EXAMPLE 196

N-piperidino-5-(4-chlorophenyl)-1-(2,4-dichlorophenyl)-4-methyl-pyrazole-3-carboxamide hydrochloride A saturated solution of gaseous HCl in ether is added dropwise to a solution of 5.9 g of the compound obtained above in 50 ml of ether until pH=1. The precipitate formed is filtered off, washed with ether and dried under vacuum to give 6.0 g of the expected hydrochloride. m.p.=224° C. (dec.).

EXAMPLE 197

N-piperidino-5-(4-chlorophenyl)-1-(2,4-dichlorophenyl)-4-methyl-pyrazole-3-carboxamide methanesulfonate A solution of 0..062 g of methanesulfonic acid in 2 ml of acetone is added dropwise to a solution of 0.30 g of the compound obtained in example 195 in 3 ml of acetone. The white crystals formed upon cooling to 0° C. are filtered off, washed with acetone and dried under vacuum to give 0.30 g of the expected salt. m.p.=218° C.

EXAMPLE 198

N-piperidino-5-(4-chlorophenyl)-1-(2,4-dichlorophenyl)-4-methyl-pyrazole-3-carboxamide hemifumarate A solution of 0.038 g of fumaric acid in 6 ml of acetone is added dropwise to a solution of 0.30 g of the compound obtained in example 195 in 3 ml of acetone. The white crystals formed upon cooling to 0° C. are filtered off, washed with acetone and dried under vacuum to give 0.23 g of the expected salt. m.p.=168° C.

EXAMPLE 199

N-piperidino-5-(4-chlorophenyl)-1-(2,4-dichlorophenyl)-4-methyl-pyrazole-3-carboxamide hydrogensulfate 0.018 ml of concentrated sulfuric acid are added to a solution of 0.30 g of the compound obtained in example 195 in 3 ml of acetone. The white crystals formed are filtered off, washed with acetone and then ether, and dried under vacuum to give 0.31 g of the expected salt. m.p.=240° C.

EXAMPLE 200

N-piperidino-5-(4-chlorophenyl)-1-(2,4-dichlorophenyl)-4-methyl-pyrazole-3-carboxamide paratoluenesulfonate A solution of 0,123 g of paratoluenesulfonic acid in 6 ml of acetone is added dropwise to a solution of 0.30 g of the compound obtained in example 195 in 3 ml of acetone. The white crystals formed are filtered off, washed with acetone and dried under vacuum to give 0.34 g of the expected salt. m.p.=226° C.

The compounds described in Table XX below are prepared by the procedure of example 1 ($R_4$=H) or example 153 ($R_4$=$CH_3$)

TABLE XX

[Structure: pyrazole with $R_4$ at position 4, C(O)NHR_2 at position 3, 4-chlorophenyl at position 5, 2,4-dichlorophenyl at N-1, ·HCl]

| EXAMPLE | $R_4$ | $R_2$ | m.p.; °C. |
|---|---|---|---|
| 201 | H | —N(norbornyl, 2-azabicyclic) | 225 |
| 202 | H | —N(2-azabicyclo[2.2.2]octyl) | 230 |
| 203 | $CH_3$ | —N(4-methylpiperidinyl)—$CH_3$ | 236 |
| 204 | $CH_3$ | —N(4-benzylpiperidinyl)—$CH_2$—Ph | 138 (dec.) |
| 205 | $CH_3$ | —N(2-azabicyclo[2.2.1]heptyl) | 225 |
| 206 | $CH_3$ | —N(pyrrolidinyl) | 237 |
| 207 | $CH_3$ | —N(hexamethyleneimino) | 220 |
| 208 | $CH_3$ | —N(morpholino)—O | 223 |

The preparation of 5-(4-chlorophenyl)-1-(2,4-dichlorophenyl)-4-methylpyrazole-3-carboxylic acid, already described in example 195, steps A–C, can be improved using for example the operating conditions described in examples 209 and 210 below:

EXAMPLE 209

5-(4-chlorophenyl)-1-(2,4-dichlorophenyl)-4-methylpyrazole-3-carboxylic acid

A) Lithium salt of ethyl 4-(4-chlorophenyl)-3-methyl-4-oxydo-2-oxobuten-3-oate 2008 g of the lithium salt of hexamethyldisilazane are dissolved, in a reactor, under a nitrogen atmosphere, in 10.1

1 of methylcyclohexane. A solution of 1686 g of 4-chloropropiophenone in 4 l of methylcyclohexane is then added slowly at 20°±5° C. After stirring for 4 and a half hours, 1607 g of ethyl oxalate are added over 35 minutes at 20°±5° C. The mixture is stirred for 17 hours at the same temperature. The solid formed is filtered off, washed with methylcyclohexane and dried under vacuum to give 1931 g of the expected product.

B) 5-(4-chlorophenyl)-1-(2,4-dichlorophenyl)-4-methyl-pyrazole-3-carboxylic acid 1/ 1921 g of the lithium salt obtained above are dissolved, in a reactor, under a nitrogen atmosphere, in 11 l of EtOH. 1493 g of 2,4-dichlorophenylhydrazine hydrochloride are then immediatly added at 20°±5° C. The mixture is stirred for 1 hour and 2.88 l of deionized water are then added, and stirring is continued for 17 hours at 20°±5° C. The precipitate formed is filtered off, washed with 80 % (v/v) ethanol and dried under vacuum to give 2280 g of the expected hydrazone. M.p.=140° C.

2/ 2267 g of hydrazone are dissolved, in a reactor, under a nitrogen atmosphere, in 11.3 l of toluene. 201.6 g of paratoluenesulfonic acid are then added and the mixture is refluxed for 3 hours. The mixture is cooled to 20°±5° C. and paratoluenesulfonic acid is removed by extraction with deionized water. 120.75 g of benzyltriethylammonium chloride and then a solution of 636 g of NaOH in 1180 ml of deionized water are added to the toluene solution. The mixture is heated for 4 hours at 68°±3° C. with vigorous stirring, sodium hydroxide is then neutralized and the reaction mixture is acidified with 1500 ml of HCl (d=1.19). The mixture is cooled to 20°±5° C., the precipitate formed is filtered off, washed with toluene and then deionized water, and dried under vacuum to give 1585 g of the expected product. M.p.=210° C.

EXAMPLE 210

5-(4-chlorophenyl)-1-(2,4-dichlorophenyl)-4-methylpyrazole-3-carboxylic acid

A) 1-(4-chlorophenyl)-1-trimethylsilyloxypropene 13.47 g of chlorotrimethylsilane are slowly added to 12.55 g of triethylamine, under a nitrogen atmosphere, at 20°±3° C. 16.86 g of 4-chloropropiophenone (endothermic mixture) and then a solution of 18.58 g of sodium iodide in 125 ml of acetonitrile are further added while maintaining the temperature at 18°±2° C. The mixture is then heated for 3 hours at 40°±5° C., the acetonitrile is removed under reduced pressure and 150 ml of toluene are added to the solid residue. 50 ml of solvent are distilled under reduced pressure to drive the residual acetonitrile off. The inorganic materials are extracted with 100 ml of iced water, the organic phase is washed with 100 ml of iced water and dried over magnesium sulfate. The toluene is removed under reduced pressure and complete removal of the solvents is performed for 15 hours at 60° C. under a pressure of 1 mbar to give 22.7 g of an oil. NMR run at 200 MHz (CDCl$_3$) 0.13 ppm:s:9H 1.7 ppm:d:3H 5.28 ppm:q:1H 7.21–7.39 ppm:m:4H.

B) Ethyl 3-(4-chlorobenzoyl)-3-methylpyruvate 10 g of anhydrous zinc chloride are suspended in 50 ml of toluene under a nitrogen atmosphere. Residual water is azeotropically driven off over 1 hour under atmospheric pressure. 20 ml of toluene and then 11.5 ml of ethyl ether are added to the mixture, cooled to 20°±3° C. A solution of 17 g of ethyl chloroglyoxylate diluted in 20 ml of dichloromethane is then slowly added to the mixture cooled to 0°±2° C. 14.5 g of the product obtained in the previous step are added over 1 and a half hours at the same temperature. The temperature is then allowed to rise to RT and the mixture is heated for 4 hours at 45° C. The organic phase is washed with a solution of sodium hydrogen-carbonate and then water, and dried over magnesium sulfate. The solvents are removed under reduced pressure to give 17.6 g of an oil. NMR run at 200 MHz (CDCl$_3$) 1.25 ppm:t:3H 1.35 ppm:d:3H 4.20 ppm:q:2H 4.93 ppm:q:1H 7.45–7.90 ppm m:4H.

C) Ethyl 5-(4-chlorophenyl)-1-(2,4-dichlorophenyl)-4-methylpyrazole-3-carboxylate 13.3 g of 2,4-dichlorophenylhydrazine hydrochloride are added to 17.6 g of the compound obtained in the previous step and the mixture is stirred for 18 hours at 20°±3° C. Without isolating the hydrazone, 0.56 g of paratoluenesulfonic acid are then added and the ternary azeotrope (water, ethanol, toluene) is distilled. Toluene reflux is continued for 1 hour and the reaction mixture is then cooled to 20°±3° C. The insoluble material is filtered off and the toluene solution is then washed twice with 100 ml of water. The solvents are removed under reduced pressure to give a crude oil which is used as such in the next step.

D) 5-(4-chlorophenyl)-1-(2,4-dichlorophenyl)-4-methyl-pyrazole-3-carboxylic acid 8.1 g of KOH in pellets are added to a solution of the oil obtained in the previous step in 100 ml of MeOH. The mixture is left for 1 hour at 25°±3° C. and the solvents are then removed under reduced pressure. The residue is taken up with 200 ml of water and 40 ml of toluene, the mixture is heated at 60°±3° C., decanted, and the aqueous phase is extracted three times, at this temperature, with 40 ml of toluene. Hydrochloric acid is then added to the aqueous phase until pH=1.5. The white crystals formed are filtered off, washed with water and then iso ether and dried under vaccum to give 9.9 g of the expected product. M.p.=210° C.

The compound of example 195 can also be prepared using operating conditions which are industrially more accessible, as described in example 211 below:

EXAMPLE 211

N-piperidino-5-(4-chlorophenyl)-1-(2,4-dichlorophenyl)-4-methylpyrazole-3-carboxamide A suspension of 1568.6 g of the acid obtained in step B of example 209 in 14.1 l of methylcyclohexane is heated, under a nitrogen atmosphere, to 83°±3° C., and a solution of 554.5 g of thionyl chloride in 1.57 l of methylcyclohexane is added thereto. The mixture is stirred for 3 hours at 83°±3° C. and the temperature is then increased over 2 hours up to the reflux temperature of methylcyclohexane while removing the excess thionyl chloride by distillation. The mixture is cooled to 10°±3° C. and a solution of 452.9 g of 1-aminopiperidine and 457.5 g of triethylamine in 3.14 l of THF is then slowly added. The mixture is stirred for 17 hours while alllowing the temperature to rise to 20°±5° C., and the organic phase is successively washed, at 20°±5° C., with deionized water and a 4% aqueous solution of acetic acid. The organic phase is then washed, at 70°±3° C., with a 1.5% solution of NaOH and then deionized water, and the THF and water are driven off by azeotropic distillation under atmospheric pressure. The mixture is allowed to cool to 20°±5° C. The expected product crystallises, the precipate formed is filtered off, washed with methylcyclohexane and dried under vaccum to give 1627 g of the title compound. DSC: endothermic peak centered at 155.5° C.

EXAMPLE 212

N-piperidino-5-(4-chlorophenyl)-1-(2,4-dichlorophenyl)-4-methylpyrazole-3-carboxamide (solvate with ethanol)

10 g of the compound obtained in example 195 are suspended in 60 ml of absolute ethanol and the mixture is refluxed until complete dissolution of the compound. The mixture is allowed to cool to 20°±3° C. and stirring is continued for 2 hours. The white crystals formed are filtered off, washed with ethanol and dried under vacuum to give 9.6 g of the expected product. DSC: endothermic peak centered at 102.7° C. % calculated C: 56.5 H: 5.29 N: 10.98 % found C: 56.43 H: 5.41 N: 11.05.

EXAMPLE 213

N-piperidino-5-(4-chlorophenyl)-1-(2,4-dichlorophenyl)-4-methylpyrazole-3-carboxamide hydrochloride (solvate with ethanol)

40 g of the compound obtained in example 196 are suspended in 400 ml of absolute ethanol. The mixture is heated to the boiling point until complete dissolution of the compound and then stirred for 20 hours while progressively cooling it to 20°±3° C. The white crystals formed are filtered off, washed with ethanol and dried under vacuum to give 29.6 g of the expected product. DSC: broad endothermic peak (175°–230° C.) Thermogravimetry: weight loss:about 8.2% starting at 100° C.

| % calculated | C: 53.04 | H: 5.16 | N: 10.31 |
| % found | C: 52.68 | H: 5.23 | N: 10.34. |

EXAMPLE 214

N-piperidino-5-(4-chlorophenyl)-1-(2,4-dichlorophenyl)-4-methylpyrazole-3-carboxamide methanesulfonate (hemisolvate with acetone)

3.84 g of methanesulfonic acid are added at 20°±3° C. to a solution of 18.55 g of the compound obtained in example 195 in 185 ml of acetone and the mixture is stirred for 20 hours at the same temperature. The white crystals formed are filtered off, washed with acetone and dried under vacuum to give 21.65 g of the expected product. DSC: melting, recrystallisation at about 175° C. then melting at 191.5° C. Thermogravimetry: weight less:about 5.2 % starting at 90° C.

| % calculated | C: 49.90 | H: 4.75 | N: 9.50 |
| % found | C: 49.70 | H: 4.76 | N: 9.44. |

EXAMPLE 215

N-piperidino-5-(4-chlorophenyl)-1-(2,4-dichlorophenyl)-4-methylpyrazole-3-carboxamide paratoluenesulfonate 7.61 g of paratoluenesulfonic acid are added at 20°±3° C. to a solution of 18.55 g of the compound obtained in example 195 in 185 ml of acetone and the mixture is stirred for 20 hours at the same temperature. The white crystals formed are filtered off, washed with acetone and dried under vacuum to give 24.25 g of the expected product. DSC: endothermic peak centered at 236.8° C.

| % calculated | C: 54.16 | H: 4.60 | N: 8.72 |
| % found | C: 54.11 | H: 4.71 | N: 8.69. |

EXAMPLE 216

N-piperidino-5-(4-chlorophenyl)-1-(2,4-dichlorophenyl)-4-methylpyrazole-3-carboxamide dihydrogenphosphate 4.61 g of 85% phosphoric acid are added at 20°±3° C. to a solution of 18.55 g of the compound obtained in example 195 in 185 ml of methylethylketone. Water is removed by distillation under atmospheric pressure of the azeotrope methylethylketone/water. The mixture is progressively cooled to 20°±3° C. while stirring for 20 hours. The white crystals formed are filtered off, washed with methylethylketone and dried under vacuum to give 21 g of the expected product. DSC: endothermic peak centered at 185.5° C.

| % calculated | C: 47.04 | H: 4.31 | N: 9.97 |
| % found | C: 46.96 | H: 4.62 | N: 9.98. |

What is claimed is:
1. A compound of the formula

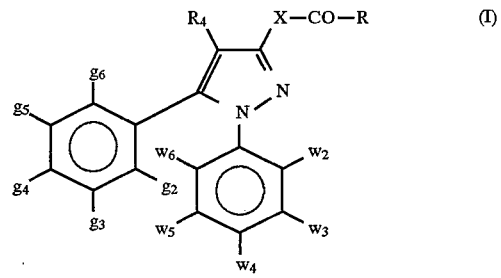

(I)

in which $g_2$, $g_3$, $g_4$, $g_5$ and $g_6$ and $w_2$, $w_3$, $w_4$, $w_5$ and $w_6$ are identical or different and are independently hydrogen, a chlorine or bromine atom, a ($C_1$–$C_3$)-alkyl, a ($C_1$–$C_3$)-alkoxy, a trifluoromethyl or a nitro group and $g_4$ is optionally a phenyl group;

$R_4$ is hydrogen or a ($C_1$–$C_3$)-alkyl;

X is either a direct bond or a group —($CH_2$)$_x$—N($R_3$)—, in which $R_3$ is hydrogen or a ($C_1$–$C_3$)-alkyl and x is zero or one; and, R is a group —$NR_1R_2$ in which $R_1$ and $R_2$ are independently a ($C_1$–$C_6$)-alkyl; an optionally-substituted non-aromatic ($C_3$–$C_{15}$) carbocyclic radical; an amino ($C_1$–$C_4$) alkyl group in which the amino is optionally disubstituted by a ($C_1$–$C_3$)-alkyl; a cycloalkyl-($C_1$–$C_3$) alkyl in which the cycloalkyl is $C_3$–$C_{12}$; a phenyl which is unsubstituted or mono-substituted or polysubstituted by a halogen, by a ($C_1$–$C_5$)-alkyl or by a ($C_1$–$C_5$)-alkoxy; a phenyl ($C_1$–$C_3$)-alkyl; a diphenyl-($C_1$–$C_3$)-alkyl; a naphthyl; an anthracenyl; a saturated 5- to 8-membered heterocyclic radical which is unsubstituted or substituted by a ($C_1$–$C_3$)- alkyl, by a hydroxyl or by a benzyl group; a 1-adamantylmethyl; an aromatic heterocycle unsubstituted, mono- or polysubstituted by a halogen, a ($C_1$–$C_5$)-alkyl, a ($C_1$–$C_5$)-alkoxy; a ($C_1$–$C_3$)-alkyl substituted by an aromatic heterocycle unsubstituted or mono- or polysubstituted by a halogen, a ($C_1$–$C_5$) alkyl, a ($C_1$–$C_5$)-alkoxy, or else $R_1$ is hydrogen and $R_2$ is as defined above, or else $R_1$ and $R_2$, together with the nitrogen atom to which they are bonded, form a saturated 5- to 8-membered heterocyclic radical, said heterocyclic radical being other than morpholine when $w_2$, $w_3$, $w_4$, $w_5$ and $w_6$ and $g_2$, $g_3$, $g_4$, $g_5$ and $g_6$ are all hydrogen;

a group $R_2$ as defined above when X is —($CH_2$)$_x$N($R_3$)—; or a group $R_5$ when X is a direct bond, $R_5$ being a ($C_1$–$C_3$)-alkyl; a ($C_3$–$C_{12}$)-cycloalkyl which is unsubstituted or substituted by a ($C_1$–$C_5$)-alkyl; a phenyl-($C_1$–$C_3$)-alkyl which is unsubstituted or substituted by a halogen or by a ($C_1$–$C_5$)-alkyl; a cycloalkyl-($C_1$–$C_3$)-alkyl in which the cycloalkyl is $C_3$–$C_{12}$ and is unsubstituted or substituted by a ($C_1$–$C_5$)-alkyl; or a 2-norbornylmethyl;

or one of its salts.

2. A compound according to claim 1 of the formula

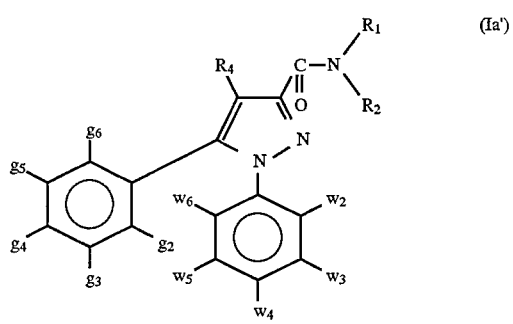

in which $w_2$, $w_3$, $w_4$, $w_5$ and $w_6$, $g_2$, $g_3$, $g_4$, $g_5$ and $g_6$ and $R_4$ are as defined for (I) in claim 1, $R_1$ is hydrogen or a ($C_1$–$C_6$)-alkyl and $R_2$ is a non-aromatic ($C_3$–$C_{15}$) carbocyclic radical or a saturated 5- to 8-membered heterocyclic radical selected from 1-pyrrolidinyl, 1- piperidinyl, 1-hexahydroazepinyl, 4-morpholinyl and 4-thiomorpholinyl, or one of its salts.

3. A compound according to claim 1 of the formula

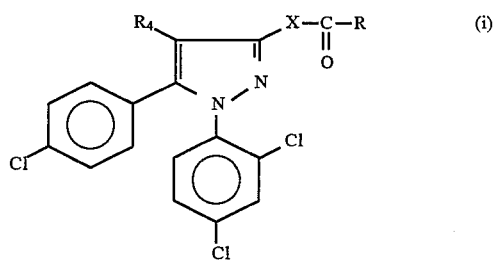

in which $R_4$, X and R are as defined for (I) in claim 1, or one of its salts.

4. A compound of formula (i) according to claim 3 in which $R_4$ is hydrogen or a methyl group, or one of its salts.

5. A compound of formula (i) according to claim 3 in which $R_4$ is hydrogen or methyl and X is a direct bond, or one of its salts.

6. A compound of formula (i) according to claim 3 in which $R_4$ is hydrogen or methyl, X is a direct bond and R is a group —$NR_1R_2$ in which $R_1$ is hydrogen or a methyl group and $R_2$ is a non-aromatic $C_3$–$C_{15}$ carbocyclic radical or a saturated 5- to 8-membered heterocyclic radical selected from 1-pyrrolidinyl, 1-piperidinyl, 1-hexahydroazepinyl, 4-morpholinyl and 4-thiomorpholinyl, or one of its salts.

7. A compound which is N-piperidino-5-(4-chlorophenyl)-1-(2,4-dichlorophenyl)-4-methyl-pyrazole-3-carboxamide, or one of its salts or solvates thereof.

8. A compound according to claim 7 wherein said salts or solvates are selected from the group consisting of the hydrochloride or its solvate with ethanol, the methanesulfonate or its hemisolvate with acetone, the hemifumarate, the hydrogensulfate, the paratoluenesulfonate and the dihydrogenphosphate.

9. A compound of formula (i) according to claim 3 in which $R_4$ is hydrogen or methyl, X is —($CH_2$)$_x$—N($R_3$)— and R is —$NR_1R_2$, x is zero or one, $R_3$ is hydrogen or a methyl group, $R_1$ is hydrogen and $R_2$ is a phenyl which is unsubstituted or substituted by one or two halogen atoms, a ($C_1$–$C_5$)-alkyl group or a ($C_1$–$C_5$)-alkoxy group, or a non-aromatic ($C_3$–$C_{15}$) carbocyclic radical, or one of its salts.

10. A compound according to claim 1 of the formula

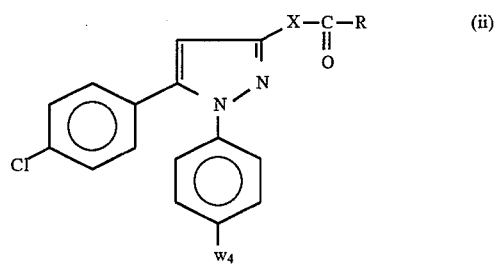

in which X and R are as defined for (I) in claim 1 and $w_4$ is a methyl group or a methoxy group, or one of its salts.

11. A compound of formula (ii) according to claim 10 in which $w_4$ is methyl or methoxy, X is a direct bond and R is a group —$NR_1R_2$ in which $R_1$ is hydrogen or a methyl group and $R_2$ is a non-aromatic ($C_3$–$C_{15}$) carbocyclic radical, or one of its salts.

12. A compound of formula (ii) according to claim 10 in which $w_4$ is methyl or methoxy, X is a group —($CH_2$)$_x$—N($R_3$)— in which x is zero or one and $R_3$ is hydrogen or a methyl group, and R is a group —$NR_1R_2$ in which $R_1$ is hydrogen and $R_2$ is a phenyl which is unsubstituted or substituted by one or two halogen atoms, a ($C_1$–$C_5$)-alkyl group or a ($C_1$–$C_5$)-alkoxy group, or a non-aromatic ($C_3$–$C_{15}$) carbocyclic radical, or one of its salts.

13. A compound of formula (I) according to claim 1 in which $w_2$, $w_3$, $w_4$, $w_5$ and $w_6$, $g_2$, $g_3$, $g_4$, $g_5$ and $g_6$ and $R_4$ and X are as defined for (I) in claim 1 and R is a group —$NR_1R_2$ in which $R_1$ is hydrogen or a ($C_1$–$C_6$)-alkyl group and $R_2$ is a 2- or 3-indolyl-($C_1$–$C_3$)-alkyl group or a 2- or 3-indolyl group, or one of its salts.

14. A compound according to claim 1 of the formula

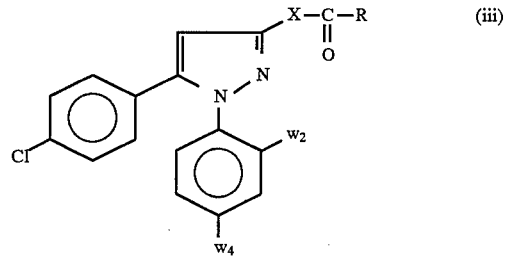

in which X is as defined for (I) in claim 1, R is a group —$NR_1R_2$ in which $R_1$ is hydrogen or a ($C_1$–$C_6$)-alkyl and $R_2$ is a 2- or 3-indolyl-$(C_1-C_3)$-alkyl group or a 2or 3-indolyl group, and either $w_2$ is hydrogen and $w_4$ is a methyl or methoxy group or $w_2$ and $w_4$ are a chlorine atom, or one of its salts.

15. A compound according to claim 1 of the formula

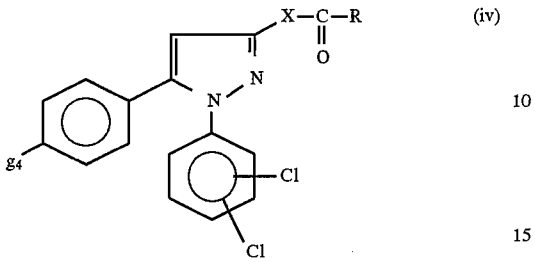

in which X and R are as defined for (I) in claim 1 and $g_4$ is a bromine atom or a methyl or trifluoromethyl group, or one of its salts.

16. A compound of the formula

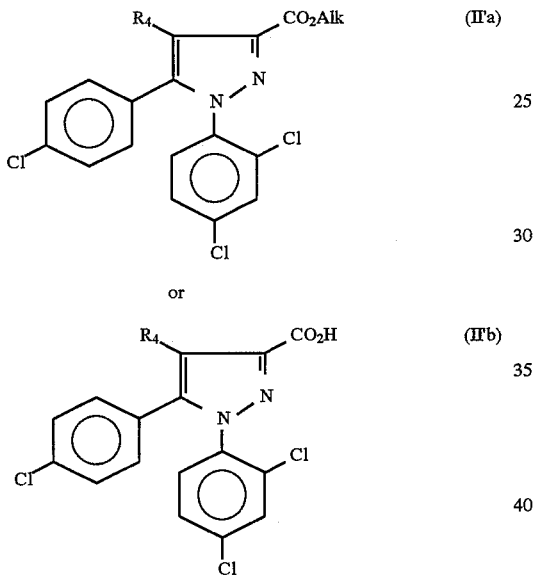

in which $R_4$ is as defined for (I) in claim 1 and Alk is a $(C_1-C_5)$-alkyl.

17. A pharmaceutical composition containing a pharmaceutically effective amount of a compound of formula (I) according to claim 1 or one of its pharmaceutically acceptable salts, mixed with at least one pharmaceutically acceptable excipient.

18. A pharmaceutical composition according to claim 17, which is in the form of a dosage unit.

19. A pharmaceutical composition according to claim 18, containing from 0.5 to 1000 mg of active principle.

20. A pharmaceutical composition according to claim 17, wherein the active principle is N-piperidino-5-(4-chlorophenyl)-1-(2,4-dichlorophenyl)-4-methyl-pyrazole-3-carboxamide, or one of its pharmaceutically acceptable salts or solvates thereof.

21. A compound according to claim 1, wherein:

$g_2$, $g_3$, $g_4$, $g_5$ and $g_6$ and $w_2$, $w_3$, $w_4$, $w_5$ and $w_6$ are identical or different and are independently hydrogen, a chlorine or bromine atom, a $(C_1-C_3)$alkyl, a $(C_1-C_3)$ alkoxy, a trifluoromethyl or a nitro group and $g_4$ is optionally a phenyl group;

$R_4$ is hydrogen or a $(C_1-C_3)$alkyl; and
either:

(a) X is a direct bond, and R is:
(i) a group —$NR_1R_2$ in which $R_1$ is hydrogen; a $(C_1-C_5)$alkyl or a non-aromatic $(C_3-C_{15})$carbocyclic radical and $R_2$ is a $(C_1-C_6)$alkyl; a non-aromatic $(C_3-C_{15})$carbocyclic radical optionally substituted by at least a $(C_1-C_5)$alkyl, a $(C_1-C_5)$alkoxy, a halogen and/or a hydroxy; an amino$(C_1-C_4)$alkyl group in which the amino is disubstituted by a $(C_1-C_3)$ alkyl; a $(C_3-C_{12})$cycloalkyl$(C_1-C_3)$alkyl; a phenyl which is unsubstituted or monosubstituted by a halogen or a $(C_1-C_5)$alkyl; a phenyl$(C_1-C_3)$alkyl; a diphenyl$(C_1-C_3)$alkyl; a saturated 5- to 8-membered heterocyclic radical selected from the group consisting of pyrrolidinyl, piperidyl, morpholinyl, hexahydroazepinyl, quinuclidinyl, oxabicycloheptanyl, azabicyclo[2.2.1]heptanyl and azabicyclo[2.2.2]octanyl, unsubstituted or substituted by a $(C_1-C_3)$alkyl or a benzyl group; or a $(C_1-C_3)$alkyl substituted by an aromatic heterocycle selected from the group consisting of pyrrolyl, pyridyl and indolyl, unsubstituted or monosubstituted by a $(C_1-C_5)$alkyl; or else $R_1$ and $R_2$, together with the nitrogen atom to which they are bonded, form a saturated 5- to 8-membered heterocyclic radical selected from the group consisting of pyrrolidinyl, piperidyl and morpholinyl, said heterocyclic radical being other than morpholine when $w_2$, $w_3$, $w_4$, $w_5$ and $w_6$ and $g_2$, $g_3$, $g_4$, $g_5$ and $g_6$ are all hydrogen; or (ii) a group $R_5$, $R_5$ being a phenyl$(C_1-C_3)$alkyl in which the phenyl is substituted by a $(C_1-C_5)$alkyl; a $(C_3-C_{12})$cycloalkyl$(C_1-C_3)$alkyl; or a 2-norbornylmethyl;

or (b) X is a group —$(CH_2)_x$—$N(R_3)$— in which $R_3$ is hydrogen or a $(C_1-C_3)$alkyl and x is zero or one and R is:

(i) a group —$NR_1R_2$ in which $R_1$ is hydrogen and $R_2$ is a non-aromatic $(C_3-C_{15})$carbocyclic radical or a phenyl which is unsubstituted or mono- or disubstituted by a halogen, a $(C_1-C_5)$alkyl or a $(C_1-C_5)$ alkoxy; or (ii) a group $R_2$, $R_2$ being a non-aromatic $(C_3-C_{15})$ carbocyclic radical; a phenyl substituted by a halogen; an anthracenyl; or an indolyl optionally substituted by a $(C_1-C_5)$alkoxy;

or one, of its salts.

22. A compound according to claim 1, wherein X is a direct bond and R represents:

(i) a group —$NR_1R_2$ in which $R_1$ is hydrogen; a $(C_1-C_6)$ alkyl or a non-aromatic $(C_3-C_{15})$carbocyclic radical and $R_2$ is a $(C_1-C_6)$alkyl; a non-aromatic $(C_3-C_{15})$ carbocyclic radical optionally substituted by at least a $(C_1-C_5)$alkyl, a $(C_1-C_5)$alkoxy, a halogen and/or a hydroxy; an amino$(C_1-C_4)$alkyl group in which the amino is disubstituted by a $(C_1-C_3)$alkyl; a $(C_3-C_{12})$ cycloalkyl$(C_1-C_3)$alkyl; a phenyl which is unsubstituted or monosubstituted by a halogen or a $(C_1-C_5)$ alkyl; a phenyl$(C_1-C_3)$alkyl; or a diphenyl$(C_1-C_3)$ alkyl; or (ii) a group $R_5$, $R_5$ being a phenyl$(C_1-C_3)$alkyl in which the phenyl is substituted by a $(C_1-C_5)$alkyl; a $(C_3-C_{12})$ cycloalkyl$(C_1-C_3)$alkyl; or a 2-norbornylmethyl;

or one of its salts.

23. A compound according to claim 1, wherein X is a direct bond and R represents a group —$NR_1R_2$ in which $R_1$ is hydrogen; a $(C_1-C_6)$alkyl or a non-aromatic $(C_3-C_{15})$ carbocyclic radical and $R_2$ is a saturated 5- to 8-membered heterocyclic radical selected from the group consisting of pyrrolidinyl, piperidyl, morpholinyl, hexahydroazepinyl, quinuclidinyl, oxabicycloheptanyl, azabicyclo[2.2.1]heptanyl and azabicyclo[2.2.2]octanyl, unsubstituted or substituted by a $(C_1-C_3)$alkyl or a benzyl group; or else $R_1$ and $R_2$, together with the nitrogen atom to which they are bonded, form a saturated 5- to 8-membered heterocyclic radical selected from the group consisting of pyrrolidinyl, piperidyl and morpholinyl, said heterocyclic radical being other than morpholine when $w_2$, $w_3$, $w_4$, $w_5$ and $w_6$ and $g_2$, $g_3$, $g_4$, $g_5$ and $g_6$ are all hydrogen;

or one of its salts.

24. A compound according to claim 1, wherein X is a direct bond and R represents a group $-NR_1R_2$ in which $R_1$ is hydrogen; a $(C_1-C_6)$alkyl or a non-aromatic $(C_3-C_{15})$ carbocyclic radical and $R_2$ is a $(C_1-C_3)$alkyl substituted by an aromatic heterocycle selected from the group consisting of pyrrolyl, pyridyl and indolyl, unsubstituted or monosubstituted by a $(C_1-C_5)$alkyl; or one of its salts.

25. A compound according to claim 1, wherein X is a group $-(CH_2)_x-N(R_3)-$ in which $R_3$ is hydrogen or a $(C_1-C_3)$alkyl and x is zero or one and R is:

(i) a group $-NR_1R_2$ in which $R_1$ is hydrogen and $R_2$ is a non-aromatic $(C_3-C_{15})$carbocyclic radical or a phenyl which is unsubstituted or mono- or disubstituted by a halogen, a $(C_1-C_5)$alkyl or a $(C_1-C_5)$alkoxy; or (ii) a group $R_2$, $R_2$ being a non-aromatic $(C_3-C_{15})$ carbocyclic radical; a phenyl substituted by a halogen; an anthracenyl; or an indolyl optionally substituted by a $(C_1-C_5)$alkoxy;

or one of its salts.

26. A pharmaceutical composition according to claim 18, wherein the active princiiple is N-piperidino-5-(4-chlorophenyl)-1-(2,4-dichlorophenyl)-4-methylpyrazole-3-carboxamide, or one of its pharmaceutically acceptable salts or a solvate thereof.

27. A pharmaceutical composition according to claim 19, wherein the active principle is N-piperidino-5-(4-chlorophenyl)-1-(2,4-dichlorophenyl)-4-methylpyrazole-3-carboxamide, or one of its pharmaceutically acceptable salts or a solvate thereof.

28. A pharmaceutical composition containing a pharmaceutically effective amount of a compound of formula (I) according to claim 1, or one of its pharmaceutically acceptable salts, mixed with at least one pharmaceutically acceptable excipient.

29. A pharmaceutical composition according to claim 29 which is in the form of a dosage unit.

30. A pharmaceutical composition according to claim 29 containing from 0.5 to 1000 mg of active principle.

* * * * *

UNITED STATES PATENT AND TRADEMARK OFFICE
CERTIFICATE OF CORRECTION

PATENT NO. : 5,624,941
DATED : April 29, 1997
INVENTOR(S) : Barth et al.

It is certified that error appears in the above-identified patent and that said Letters Patent is hereby corrected as shown below:

Column 2,
Line 63, delete "substiituent(s)" and insert -- substituent(s) --.

Column 3,
Line 37, delete "Group" and insert -- group --.

Column 7,
Line 48, delete "carlDon" and insert -- carbon --.

Column 11,
The portion of formula IV that reads:

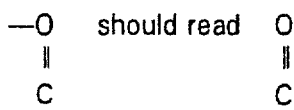

Column 12,
Line 45, the portion of formula (II'a) that reads "ou" should be deleted.

Column 13,
Line 39, delete "(2,4-dichlorophenyl" and insert -- (2,4-dichlorophenyl) --.

Column 17,
Line 45, the portion of formula (VIIc) that reads "g₅" should read -- $R_4$ --.

Column 22,
The portion of Route 1 that reads:

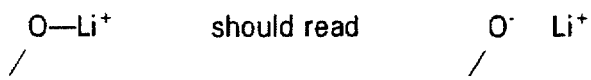

Column 24,
Line 67, delete "945" and insert -- 1945 --.

Column 25,
Line 27, delete "[2.2.21]" and insert -- [2.2.2] --.
Line 37, delete "72" and insert -- 1972 --.
Line 46, delete "65" and insert -- 1965 --.

UNITED STATES PATENT AND TRADEMARK OFFICE
CERTIFICATE OF CORRECTION

PATENT NO. : 5,624,941
DATED : April 29, 1997
INVENTOR(S) : Barth et al.

It is certified that error appears in the above-identified patent and that said Letters Patent is hereby corrected as shown below:

Column 26,
Line 40, before "$w_2$" insert -- $g_4$ --.

Column 27,
Line 50, delete the hyphen (-) between "methyl-paraben".
Line 54, delete the hyphen (-) between "polyvinyl-pyrrolidone".

Column 28,
Line 51, delete "psychotic" and insert -- psychotropic --.

Column 29,
Line 43, delete "32" and insert -- = --.
Line 65, delete "according to".
Line 65, delete "83" and insert -- 1983 --.

Column 30,
Line 41, delete "solultion" and insert -- solution --.
Line 66, delete " the" and insert -- then --.

Column 31,
Line 16, insert -- (I): $w_2$, $w_4$ = Cl; $g_4$ = Cl; $R_4$ = H; --.

Column 32,
Line 2, delete "01.30" and insert -- 0.30 --.
Line 21, insert -- (I): $w_2$, $w_4$ = Cl; $g_4$ = Cl; $R_4$ = H; --.

Column 35,
In "Example n°" insert -- 15 -- between "14 and 16".

Column 64,
Line 1, insert -- (I): $g_4$ = Cl; $w_2$, $w_4$ = Cl; $R_4$ = $CH_3$; --.

Column 65,
Line 36, insert -- (I): $g_4$ = Cl; $w_4$ = $CH_3$; $R_4$ = H; --.
Line 47, after "in" insert -- 5 --.
Line 49, after "for" insert -- 2 --.

Column 68,
Line 38, insert -- (I): $g_4$ = Cl; $w_2$, $w_4$ = Cl; $R_4$ = H; --.

UNITED STATES PATENT AND TRADEMARK OFFICE
CERTIFICATE OF CORRECTION

PATENT NO. : 5,624,941  
DATED : April 29, 1997  
INVENTOR(S) : Barth et al.

Page 3 of 4

It is certified that error appears in the above-identified patent and that said Letters Patent is hereby corrected as shown below:

Column 71,  
Line 1, insert -- (I): $g_4$ = Cl; $w_2$, $w_4$ = Cl; $R_4$ = H; --.  
Line 49, insert -- (I): $w_2$ = $w_4$ = Cl; $g_4$ = Cl; $R_4$ = H; --.

Column 73,  
Lines 1 and 29, insert -- (I): $w_2$ = $w_4$ = Cl; $g_4$ = Cl; $R_4$ = H; --.

Column 74,  
Lines 31 and 57, insert -- (I): $g_4$ = Cl; $w_2$, $w_4$ = Cl; $R_4$ = H; --.

Column 75,  
Line 14, delete "292" and insert -- 192 --.  
Line 24, delete "liltrate" and insert -- filtrate --.

Column 76,  
Line 30, delete "08.8g" and insert -- 8.8g --.  
Line 41, delete "1(2,4-" and insert -- 1-(2,4- --.

Column 77,  
Line 9, delete "0..062g" and insert -- 0.062g --.  
Line 58, delete "0,123g" and insert -- 0.123g --.

Column 80,  
Line 8, delete the hyphen (-) between "hydrogen-carbonate".  
Line 62, delete "allLowing" and insert -- allowing --.

Column 83,  
Line 26, the title of this formula that reads "(la')" should read -- (la) --.

Column 85,  
Line 1, Delete "2or" and insert -- 2- or --.

Column 86,  
Line 3, delete "$C_5$" and insert -- $C_6$ --.  
Line 47, delete the comma (,) between "one" and "of".  
Lines 48 and 65, delete "1" and insert -- 21 --.

Column 87,  
Lines 14 and 21, delete "1" and insert -- 21 --.

UNITED STATES PATENT AND TRADEMARK OFFICE
CERTIFICATE OF CORRECTION

PATENT NO. : 5,624,941
DATED : April 29, 1997
INVENTOR(S) : Barth et al.

It is certified that error appears in the above-identified patent and that said Letters Patent is hereby corrected as shown below:

<u>Column 88,</u>
Line 7, delete "princiiple" and insert -- principle --.
Line 19, delete "1" and insert -- 21 --.
Line 22, delete "29" and insert -- 28 --.

Signed and Sealed this

Ninth Day of April, 2002

Attest:

Attesting Officer

JAMES E. ROGAN
Director of the United States Patent and Trademark Office